(12) United States Patent
Koh

(10) Patent No.: US 7,081,443 B2
(45) Date of Patent: Jul. 25, 2006

(54) CHIMERIC COMP-ANG1 MOLECULE

(75) Inventor: Gou Young Koh, Pohang (KR)

(73) Assignee: Korea Advanced Institutes of Science and Technology (Kaist), Daejeon (KR)

( * ) Notice: Subject to any disclaimer, the term of this patent is extended or adjusted under 35 U.S.C. 154(b) by 613 days.

(21) Appl. No.: 10/273,180

(22) Filed: Oct. 18, 2002

(65) Prior Publication Data

US 2003/0220476 A1    Nov. 27, 2003

Related U.S. Application Data

(60) Provisional application No. 60/382,541, filed on May 21, 2002.

(51) Int. Cl.
*C07K 14/515* (2006.01)
*A61K 38/18* (2006.01)

(52) U.S. Cl. .................. 514/2; 514/8; 514/12; 530/350; 530/402; 530/399; 530/351

(58) Field of Classification Search .............. 530/350, 530/402, 399, 351
See application file for complete search history.

(56) References Cited

U.S. PATENT DOCUMENTS

| 4,810,643 A | 3/1989 | Souza |
| 5,332,671 A | 7/1994 | Ferrara et al. |
| 6,455,035 B1 | 9/2002 | Suri et al. |

FOREIGN PATENT DOCUMENTS

| EP | 0 550 296 A3 | 7/1993 |
| WO | WO 91/05795 | 5/1991 |
| WO | WO 95/19985 | 7/1995 |
| WO | WO96/11269 | 4/1996 |
| WO | WO 96/16989 A1 | 6/1996 |
| WO | WO 96/31598 | 10/1996 |
| WO | WO 98/05779 | 2/1998 |
| WO | WO 00/37642 | 6/2000 |
| WO | WO/00/44908 * | 8/2000 |
| WO | WO 01/47951 A2 | 7/2001 |
| WO | WO 02/02746 A2 | 1/2002 |
| WO | WO 02/070725 A1 | 9/2002 |
| WO | WO 03/048185 A2 | 6/2003 |

OTHER PUBLICATIONS

Terskikh et al. (1997) Proc. Natl. Acad. Sci. USA. vol. 94, pp. 1663-1668.*
van der Geer et al., 1994, *Annu Rev Cell Biol.* 10:251-337.
Dumont et al., 1993, *Oncogene* 8:1293-1301.
Mustonen and Alitalo, 1995, *J Cell Biol.* 129:895-898.
Sato et al., 1995, *Nature* 376:70-74.
Davis et al., 1996, *Cell* 87:1161-1169.
Yancopoulos et al., 2000, *Nature* 407:242-248.
Thurston et al., 2000, *Nat. Med.* 6:460-463.
Chae et al., 2000, *Arterioscler: Thromb. Vasc. Biol.* 20:2573-2578.
Kwak et al., 2000, *Circulation* 101:2317-2324.
Maisonpierre et al., 1997, *Science* 277:55-60.
Valenzuela et al., 1999, *Proc Natl Acad Sci.* 96:1904-1909.
Jones et al., 1999, *J Biol Chem.* 274:30896-30905.
Koulos et al., 1998, *Mol Cell Biol.* 18:4131-4140.
Kim et al., 2000, *Circ Res.* 86:24-29.
Kim et al., 2000, *Circ Res.* 86:952-959.
Jones and Dumont, 1998, 17:1097-1108.
Master et al., 2001, *EMBO J.* 20:5919-5928.
Korpelainen et al., 1999, *Oncogene* 18:1-8.
Iwama et al., 1993, *Biochem Biophys Res Commun* 195:301-309.
Takakura et al., 2000, *Cell* 102:199-209.
Ellenberger et al., 1992, *Cell* 71:1223-1237.
Skehel and Wiley, 1998, *Cell* 95:871-874.
Paulsson and Heinegård, 1981, *Biochem J.* 197:367-375.
Kiss et al., 1989, *J. Biol. Chem.* 264:8126-8134.
Hauser and Paulsson, 1994, *J. Biol. Chem.* 269:25747-25753.
Hedbom et al., 1992, *J. Biol. Chem* 267:6132-6136.
Cohen and Parry, 1994, *Science* 263:488-489.
Malashkevich et al., 1996, *Science* 274:761-765.
Bermoist and Chambon, 1981, *Nature* 290:304-310.
Yamamoto, et al., 1980, *Cell* 22:787-797.
Wagner et al., 1981, *Proc. Natl. Acad. Sci. U.S.A.* 78:1441-1445.
Brinster et al., 1982, *Nature* 296:39-42.
DeBoer, et al., 1983, *Proc. Natl. Acad. Sci. U.S.A.* 80:21-25.
Gilber and Villa-Komaroff, 1980, *Scientific American* 242:74-94.
Swift et al., 1984, *Cell* 38:639-646.
Hanahan, 1985, *Nature* 315:115-122
Grosschedl et al., 1984, *Cell* 38:647-658.
Adams et al., 1985, *Nature* 318:533-538.
Alexander et al., 1987, *Mol. Cell. Biol.* 7:1436-1444.
Leder et al., 1986, *Cell* 45:485-495.
Pinkert et al., 1987, *Genes and Devel.* 1:268-276.
Krumlauf et al., 1985, *Mol. Cell. Biol.* 5:1639-1648.
Hammer et al., 1987, *Science* 235:53-58.
Kelsey et al., 1987, *Genes and Devel.* 1:161-171.
Magram et al., 1985, *Nature* 315:338-340.
Kollias et al., 1986, *Cell* 46:89-94.

(Continued)

*Primary Examiner*—Prema Mertz
(74) *Attorney, Agent, or Firm*—JHK Law; Joseph Hyosuk Kim

(57) ABSTRACT

The present application describes a fusion molecule that includes coiled coil domain, which renders the molecule soluble and provides potent activity.

4 Claims, 22 Drawing Sheets

OTHER PUBLICATIONS

Readhead et al., 1987, *Cell* 48:703-712.
Shani, 1985, *Nature* 314:283-286.
Mason et al., 1986, *Science* 234:1372-1378.
Ornitz et al., 1986, *Cold Spring Harbor Symp. Quant. Biol.* 50:399-409.
MacDonald and Swift, 1998, *Int. J. Dev. Biol.* 42:983-994.
Renai et al., 1994, *Circulation* 89:2183-2189.
Unger et al., 1994, *Am.J.Physiol.* 266:H1588-H1595.
Lazarous et al., 1995, *Circulation* 91:145-153.
Lee et al., 1985, *Proc. Natl. Acad. Sci. USA* 82:4360-4364.
Wong et al., 1985, *Science* 228:810-814.
Yokota et al., 1984, *Proc. Natl. Acad. Sci. USA* 81:1070-1074.
Benet and Sheiner, General principles (pp. 1-65) from *The Pharmacological Basis of Therapeutics*, Goodman and Gilman, eds. Macmillan Publishing Co, New York, (1985).
Sato and Rifkin, 1989, *J.Cell.Biol.* 109:309-315.
Procopio et al., "Angiopoietin-1 and -2 Coiled Coil Domains Mediate Distinct Homo-oligomerization Patterns, but Fibrinogen-like Domains Mediate Ligand Activity", Journal of Biological Chemistry, 1999, 274(42):30196-30201.
Davis et al., "Angiopotetins have distinct modular domains essential for receptor binding, dimerization and superclustering", Nature Structural Biology, 2003, 10(1): 38-44.

* cited by examiner

FIG. 2A

Monomeric-human Ang1

```
              10          20          30          40
         *    *    *    *    *    *    *    *    *
        ATG  TCT  GCA  CTT  CTG  ATC  CTA  GCT  CTT  GTT  GGA  GCT  GCA  GTT  GCT  GAC
        Met  Ser  Ala  Leu  Leu  Ile  Ala  Leu  Leu  Val  Gly  Ala  Ala  Val  Ala  Asp
        <—a  —a   —a   —a   —a  Preprotrypsin  —a   —a   —a  —>  <-

50          60          70          80          90
         *    *    *    *    *    *    *    *    *    *
        TAC  AAA  GAC  GAT  GAC  GAC  AAG  CTT  GTC  AAT  CTT  TGC  ACT  AAA  GAA  GGT
        Tyr  Lys  Asp  Asp  Asp  Asp  Lys  Leu  Val  Asn  Leu  Cys  Thr  Lys  Glu  Gly
        —b   —b   FLAG TAG —b  —>  <  —c  Ang1 LINKER REGION  —c   —c 100         110         120         130         140
         *    *    *    *    *    *    *    *    *
        GTT  TTA  CTA  AAG  GGA  GGA  AAA  AGA  GAG  GAA  GAG  AAA  CCA  TTT  AGA  GAC
        Val  Leu  Leu  Lys  Gly  Gly  Lys  Arg  Glu  Glu  Glu  Lys  Pro  Phe  Arg  Asp
        —c   —c   —c   Ang1 LINKER REGION  —c   —c   —c   ->  <—d   —d  -

150         160         170         180
         *    *    *    *    *    *    *    *    *
        TGT  GCA  GAT  GTA  TAT  CAA  GCT  GGT  TTT  AAT  AAA  AGT  GGA  ATC  TAC  ACT
        Cys  Ala  Asp  Val  Tyr  Gln  Ala  Gly  Phe  Asn  Lys  Ser  Gly  Ile  Tyr  Thr
        —d   —d   —d   —d   Ang1 FIBRINOGEN-LIKE DOMAIN  —d   —d   —d 190         200         210         220         230
         *    *    *    *    *    *    *    *    *    *
        ATT  TAT  ATT  AAT  AAT  ATG  CCA  GAA  CCC  AAA  AAG  GTG  TTT  TGC  AAT  ATG
        Ile  Tyr  Ile  Asn  Asn  Met  Pro  Glu  Pro  Lys  Lys  Val  Phe  Cys  Asn  Met
        —d   —d   —d   —d   Ang1 FIBRINOGEN-LIKE DOMAIN  —d   —d   —d 240         250         260         270         280
         *    *    *    *    *    *    *    *    *
        GAT  GTC  AAT  GGG  GGA  GGT  TGG  ACT  GTA  ATA  CAA  CAT  CGT  GAA  GAT  GGA
        Asp  Val  Asn  Gly  Gly  Gly  Trp  Thr  Val  Ile  Gln  His  Arg  Glu  Asp  Gly
        —d   —d   —d   —d   Ang1 FIBRINOGEN-LIKE DOMAIN  —d   —d   —d 290         300         310         320         330
         *    *    *    *    *    *    *    *    *
        AGT  CTA  GAT  TTC  CAA  AGA  GGC  TGG  AAG  GAA  TAT  AAA  ATG  GGT  TTT  GGA
        Ser  Leu  Asp  Phe  Gln  Arg  Gly  Trp  Lys  Glu  Tyr  Lys  Met  Gly  Phe  Gly
        —d   —d   —d   —d   Ang1 FIBRINOGEN-LIKE DOMAIN  —d   —d   —d
```

FIG. 2B

```
            340         350         360         370         380
         *    *    *    *    *    *    *    *    *    *
        AAT CCC TCC GGT GAA TAT TGG CTG GGG AAT GAG TTT ATT TTT GCC ATT
        Asn Pro Ser Gly Glu Tyr Trp Leu Gly Asn Glu Phe Ile Phe Ala Ile
        —d  —d  —d  —d Ang1 FIBRINOGEN-LIKE DOMAIN —d  —d  —d 390         400         410         420
         *    *    *    *    *    *    *    *    *
        ACC AGT CAG AGG CAG TAC ATG CTA AGA ATT GAG TTA ATG GAC TGG GAA
        Tyr Ser Gln Arg Gln Tyr Met Leu Arg Ile Glu Leu Met Asp Trp Glu
        —d  —d  —d  —d Ang1 FIBRINOGEN-LIKE DOMAIN —d  —d  —d 430         440         450         460         470
         *    *    *    *    *    *    *    *    *    *
        GGG AAC CGA GCC TAT TCA CAG TAT GAC AGA TTC CAC ATA GGA AAT GAA
        Gly Asn Arg Ala Tyr Ser Gln Tyr Asp Arg Phe His Ile Gly Asn Glu
        —d  —d  —d  —d Ang1 FIBRINOGEN-LIKE DOMAIN —d  —d  —d -

480         490         500         510         520
         *    *    *    *    *    *   *    *    *
        AAG CAA AAC TAT AGG TTG TAT TTA AAA GGT CAC ACT GGG ACA GCA GGA
        Lys Gln Asn Tyr Arg Leu Tyr Leu Lys Gly His Thr Gly Tyr Ala Gly
        —d  —d  —d  —d Ang1 FIBRINOGEN-LIKE DOMAIN —d  —d  —d -

530         540         550         560         570
         *    *    *    *    *    *    *    *    *    *
        AAA CAG AGC AGC CTG ATC TTA CAC GGT GCT GAT TTC AGC ACT AAA GAT
        Lys Gln Ser Ser Leu Ile Leu His Gly Ala Asp Phe Ser Thr Lys Asp
        —d  —d  —d  —d Ang1 FIBRINOGEN-LIKE DOMAIN —d  —d  —d -

580         590         600         610         620
         *    *    *    *    *    *    *    *    *    *
        GCT GAT AAT GAC AAC TGT ATG TGC AAA TGT GCC CTC ATG TTA ACA GGA
        Ala Asp Asn Asp Asn Cys Met Cys Lys Cys Ala Leu Met Leu Thr Gly
        —d  —d  —d  —d Ang1 FIBRINOGEN-LIKE DOMAIN —d  —d  —d -

630         640         650         660
         *    *    *    *    *    *    *    *    *
        GGA TGG TGG TTT GAT GCT TGT GGC CCC TCC AAT CTA AAT GGA ATG TTC
        Gly Trp Trp Phe Asp Ala Cys Gly Pro Ser Asn Leu Asn Gly Met Phe
        —d  —d  —d  —d Ang1 FIBRINOGEN-LIKE DOMAIN —d  —d  —d -
```

FIG. 2C

```
       670         680         690         700         710
        *     *     *     *     *     *     *     *     *     *
TAT ACT GCG GGA CAA AAC CAT GGA AAA CTG AAT GGG ATA AAG TGG CAC
Tyr Thr Ala Gly Gln Asn His Gly Lys Leu Asn Gly Ile Lys Trp His
----d ----d ----d ----d Ang1 FIBRINOGEN-LIKE DOMAIN ----d ----d ----d -

720         730         740         750         760
        *     *     *     *     *     *     *     *     *
TAC TTC AAA GGG CCC AGT TAC TCC TTA CGT TCC ACA ACT ATG ATG ATT
Tyr Phe Lys Gly Pro Ser Tyr Ser Leu Arg Ser Thr Thr Met Met Ile
----d ----d ----d ----d Ang1 FIBRINOGEN-LIKE DOMAIN ----d ----d ----d -

770         780
        *     *     *     *
CGA CCT TTA GAT TTT TGA
Arg Pro Leu Asp Phe  *
----d - d ----d ----d ----d >
```

FIG. 3A

GCN4-human Ang1

```
              10          20          30          40
         *    *    *    *    *    *    *    *    *
     ATG AAG ACG ATC ATC GCC CTG AGC TAC ATC TTC TGC CTG GTA TTC GCC
     Met Lys Thr Ile Ile Ala Leu Ser Tyr Ile Phe Cys Leu Val Phe Ala
     <—a  —a  —a HEMAGGLUTININ SIGNAL SEQUENCE —a  —a  —a>

50          60          70          80          90
     *    *    *    *    *    *    *    *    *    *
     GAC TAC AAG GAC GAT GAT GAC AAG GGG ATC TTA ATG AAA CAG CTG GAA
     Asp Tyr Lys Asp Asp Asp Asp Lys Gly Ile Leu Met Lys Gln Leu Glu
     <—b —b FLAG TAG —b  —b ->  # # # # #  <—c  —c  —c  —c 100         110         120         130         140
     *    *    *    *    *    *    *    *    *
     GAC AAA GTT GAA GAA CTG CTG TCT AAA AAC TAC CAC CTG GAA AAC GAA
     Asp Lys Val Glu Glu Leu Leu Ser Lys Asn Tyr His Leu Glu Asn Glu
     —c  —c  —c  —c  —c GCN4 CC DOMAIN —c  —c  —c  —c  —c 150         160         170         180         190
     *    *    *    *    *    *    *    *    *    *
     GTT GCT CGT CTG AAA AAA CTG GTT GGT GAA GGA TCC CTT GTC AAT CTT
     Val Ala Arg Leu Lys Lys Leu Val Gly Glu Gly Ser Leu Val Asn Leu
     —c  —c GCN4 CC DOMAIN—c  —c  —c -> # # #  <—d  —d  —d 200         210         220         230         240
     *    *    *    *    *    *    *    *    *    *
     TGC ACT AAA GAA GGT GTT TTA CTA AAG GGA GGA AAA AGA GAG GAA GAG
     Cys Thr Lys Glu Gly Val Leu Leu Lys Gly Gly Lys Arg Glu Glu Glu
     —d  —d  —d Ang1 LINKER REGION —d  —d  —d  —d  —d 250         260         270         280
     *    *    *    *    *    *    *    *    *
     AAA CCA TTT AGA GAC TGT GCA GAT GTA TAT CAA GCT GGT TTT AAT AAA
     Lys Pro Phe Arg Asp Cys Ala Asp Val Tyr Gln Ala Gly Phe Asn Lys
     —d  —d>  <—e  —e Ang1 FIBRINOGEN-LIKE DOMAIN —e  —e  —e 290         300         310         320         330
     *    *    *    *    *    *    *    *    *    *
     AGT GGA ATC TAC ACT ATT TAT ATT AAT AAT ATG CCA GAA CCC AAA AAG
     Ser Gly Ile Tyr Thr Ile Tyr Ile Asn Asn Met Pro Glu Pro Lys Lys
     —e  —e  —e  —e Ang1 FIBRINOGEN-LIKE DOMAIN —e  —e  —e
```

FIG. 3B

```
        340         350         360         370         380
         *           *           *           *           *
GTG TTT TGC AAT ATG GAT GTC AAT GGG GGA GGT TGG ACT GTA ATA CAA
Val Phe Cys Asn Met Asp Val Asn Gly Gly Gly Trp Thr Val Ile Gln
--e --e --e --e Ang1 FIBRINOGEN-LIKE DOMAIN --e --e --e 390         400         410         420         430
         *           *           *           *           *
CAT CGT GAA GAT GGA AGT CTA GAT TTC CAA AGA GGC TGG AAG GAA TAT
His Arg Glu Asp Gly Ser Leu Asp Phe Gln Arg Gly Trp Lys Glu Tyr
--e --e --e --e Ang1 FIBRINOGEN-LIKE DOMAIN --e --e --e 440         450         460         470         480
         *           *           *           *           *
AAA ATG GGT TTT GGA AAT CCC TCC GGT GAA TAT TGG CTG GGG AAT GAG
Lys Met Gly Phe Gly Asn Pro Ser Gly Glu Tyr Trp Leu Gly Asn Glu
--e --e --e --e Ang1 FIBRINOGEN-LIKE DOMAIN --e --e --e 490         500         510         520
         *           *           *           *
TTT ATT TTT GCC ATT ACC AGT CAG AGG CAG TAC ATG CTA AGA ATT GAG
Phe Ile Phe Ala Ile Thr Ser Gln Arg Gln Tyr Met Leu Arg Ile Glu
--e --e --e --e Ang1 FIBRINOGEN-LIKE DOMAIN --e --e --e 530         540         550         560         570
 *           *           *           *           *
TTA ATG GAC TGG GAA GGG AAC CGA GCC TAT TCA CAG TAT GAC AGA TTC
Leu Met Asp Trp Glu Gly Asn Arg Ala Tyr Ser Gln Tyr Asp Arg Phe
--e --e --e --e Ang1 FIBRINOGEN-LIKE DOMAIN --e --e --e 580         590         600         610         620
         *           *           *           *           *
CAC ATA GGA AAT GAA AAG CAA AAC TAT AGG TTG TAT TTA AAA GGT CAC
His Ile Gly Asn Glu Lys Gln Asn Tyr Arg Leu Tyr Leu Lys Gly His
--e --e --e --e Ang1 FIBRINOGEN-LIKE DOMAIN --e --e --e -

630         640         650         660         670
         *           *           *           *           *
ACT GGG ACA GCA GGA AAA CAG AGC AGC CTG ATC TTA CAC GGT GCT GAT
Thr Gly Tyr Ala Gly Lys Gln Ser Ser Leu Ile Leu His Gly Ala Asp
--e --e --e --e Ang1 FIBRINOGEN-LIKE DOMAIN --e --e --e -

680         690         700         710         720
         *           *           *           *           *
TTC AGC ACT AAA GAT GCT GAT AAT GAC AAC TGT ATG TGC AAA TGT GCC
Phe Ser Thr Lys Asp Ala Asp Asn Asp Asn Cys Met Cys Lys Cys Ala
--e --e --e --e Ang1 FIBRINOGEN-LIKE DOMAIN --e --e --e -
```

FIG. 3C

```
              730         740         750         760
       *   *   *   *   *   *   *   *   *
CTC ATG TTA ACA GGA GGA TGG TGG TTT GAT GCT TGT GGC CCC TCC AAT
Leu Met Leu Thr Gly Gly Trp Trp Phe Asp Ala Cys Gly Pro Ser Asn
—e —e —e —e Ang1 FIBRINOGEN-LIKE DOMAIN —e —e —e 770         780         790         800         810
   *   *   *   *   *   *   *   *   *   *
CTA AAT GGA ATG TTC TAT ACT GCG GGA CAA AAC CAT GGA AAA CTG AAT
Leu Asn Gly Met Phe Tyr Thr Ala Gly Gln Asn His Gly Lys Leu Asn
—e —e —e —e Ang1 FIBRINOGEN-LIKE DOMAIN —e —e —e -

820         830         840         850         860
   *   *   *   *   *   *   *   *   *
GGG ATA AAG TGG CAC TAC TTC AAA GGG CCC AGT TAC TCC TTA CGT TCC
Gly Ile Lys Trp His Tyr Phe Lys Gly Pro Ser Tyr Ser Leu Arg Ser
—e —e —e —e Ang1 FIBRINOGEN-LIKE DOMAIN —e —e —e -

870         880         890
   *   *   *   *   *   *   *
ACA ACT ATG ATG ATT CGA CCT TTA GAT TTT TGA
Thr Thr Met Met Ile Arg Pro Leu Asp Phe  *
—e Ang1 FIBRINOGEN-LIKE DOMAIN —e >
```

FIG. 4A

CMP-human Ang1

```
          10          20          30          40
           *     *     *     *     *     *     *     *
ATG AAG ACG ATC ATC GCC CTG AGC TAC ATC TTC TGC CTG GTA TTC GCC
Met Lys Thr Ile Ile Ala Leu Ser Tyr Ile Phe Cys Leu Val Phe Ala
<—a —a —a  —a HEMAGGLUTININ SIGNAL SEQUENCE —a  —a >

50          60          70          80          90
     *     *     *     *     *     *     *     *     *     *
GAC TAC AAG GAC GAT GAT GAC AAG GGG ATC TTA GAT GAA GAT CCG TGC
Asp Tyr Lys Asp Asp Asp Asp Lys Gly Ile Leu Asp Glu Asp Pro Cys
<—b—b —b FLAG TAG —b —> # # # # #  <—c —c —c —

100         110         120         130         140
  *     *     *     *     *     *     *     *     *
GAA TGC AAA AGC ATA GTG AAA TTC CAG ACC AAA GTG GAA GAA CTG ATC
Glu Cys Lys Ser Ile Val Lys Phe Gln Thr Lys Val Glu Glu Leu Ile
—c —c —c —c —c CMP CC DOMAIN —c —c —c —c —c 150         160         170         180         190
          *     *     *     *     *     *     *     *     *     *
AAC ACC CTG CAG CAG AAA CTG GAA GCG GTG GCG AAA CGT ATC GAA GCG
Asn Thr Leu Gln Gln Lys Leu Glu Ala Val Ala Lys Arg Ile Glu Ala
—c —c —c —c —c CMP CC DOMAIN —c —c —c —c —c 200         210         220         230         240
      *     *     *     *     *     *     *     *     *     *
CTG GAA AAC AAA ATC ATC GGA TCC CTT GTC AAT CTT TGC ACT AAA GAA
Leu Glu Asn Lys Ile Ile Gly Ser Leu Val Asn Leu Cys Thr Lys Glu
—c —c —c —c —> # # #  <—d— Ang1 LINKER REGION —d —

250         260         270         280
          *     *     *     *     *     *     *     *     *
GGT GTT TTA CTA AAG GGA GGA AAA AGA GAG GAA GAG AAA CCA TTT AGA
Gly Val Leu Leu Lys Gly Gly Lys Arg Glu Glu Glu Lys Pro Phe Arg
—d —d —d —d Ang1 LINKER REGION —d —d —d —> <—e 290         300         310         320         330
      *     *     *     *     *     *     *     *     *     *
GAC TGT GCA GAT GTA TAT CAA GCT GGT TTT AAT AAA AGT GGA ATC TAC
Asp Cys Ala Asp Val Tyr Gln Ala Gly Phe Asn Lys Ser Gly Ile Tyr
—e —e —e Ang1 FIBRINOGEN-LIKE DOMAIN —e —e —e —e
```

FIG. 4B

```
          340       350       360       370       380
           *    *    *    *    *    *    *    *    *
         ACT ATT TAT ATT AAT AAT ATG CCA GAA CCC AAA AAG GTG TTT TGC AAT
         Thr Ile Tyr Ile Asn Asn Met Pro Glu Pro Lys Lys Val Phe Cys Asn
         ——e ——e ——e Ang1 FIBRINOGEN-LIKE DOMAIN ——e ——e ——e ——e 390       400       410       420       430
           *    *    *    *    *    *    *    *    *    *
         ATG GAT GTC AAT GGG GGA GGT TGG ACT GTA ATA CAA CAT CGT GAA GAT
         Met Asp Val Asn Gly Gly Gly Trp Thr Val Ile Gln His Arg Glu Asp
         ——e ——e ——e Ang1 FIBRINOGEN-LIKE DOMAIN ——e ——e ——e ——e 440       450       460       470       480
           *    *    *    *    *    *    *    *    *    *
         GGA AGT CTA GAT TTC CAA AGA GGC TGG AAG GAA TAT AAA ATG GGT TTT
         Gly Ser Leu Asp Phe Gln Arg Gly Trp Lys Glu Tyr Lys Met Gly Phe
         ——e ——e ——e Ang1 FIBRINOGEN-LIKE DOMAIN ——e ——e ——e ——e 490       500       510       520
           *    *    *    *    *    *    *    *    *
         GGA AAT CCC TCC GGT GAA TAT TGG CTG GGG AAT GAG TTT ATT TTT GCC
         Gly Asn Pro Ser Gly Glu Tyr Trp Leu Gly Asn Glu Phe Ile Phe Ala
         ——e ——e ——e Ang1 FIBRINOGEN-LIKE DOMAIN ——e ——e ——e ——e 530       540       550       560       570
       *    *    *    *    *    *    *    *    *    *
     ATT ACC AGT CAG AGG CAG TAC ATG CTA AGA ATT GAG TTA ATG GAC TGG
     Ile Tyr Ser Gln Arg Gln Tyr Met Leu Arg Ile Glu Leu Met Asp Trp
     ——d ——d ——d Ang1 FIBRINOGEN-LIKE DOMAIN ——d ——d ——e ——e 580       590       600       610       620
           *    *    *    *    *    *    *    *    *
         GAA GGG AAC CGA GCC TAT TCA CAG TAT GAC AGA TTC CAC ATA GGA AAT
         Glu Gly Asn Arg Ala Tyr Ser Gln Tyr Asp Arg Phe His Ile Gly Asn
         ——e ——e ——e Ang1 FIBRINOGEN-LIKE DOMAIN ——e ——e ——e ——e 630       640       650       660       670
           *    *    *    *    *    *    *    *    *    *
         GAA AAG CAA AAC TAT AGG TTG TAT TTA AAA GGT CAC ACT GGG ACA GCA
         Glu Lys Gln Asn Tyr Arg Leu Tyr Leu Lys Gly His Thr Gly Thr Ala
         ——e ——e ——e Ang1 FIBRINOGEN-LIKE DOMAIN ——e ——e ——e ——e 680       690       700       710       720
           *    *    *    *    *    *    *    *    *    *
         GGA AAA CAG AGC AGC CTG ATC TTA CAC GGT GCT GAT TTC AGC ACT AAA
         Gly Lys Gln Ser Ser Leu Ile Leu His Gly Ala Asp Phe Ser Thr Lys
         ——e ——e ——e Ang1 FIBRINOGEN-LIKE DOMAIN ——e ——e ——e ——e
```

FIG. 4C

```
            730         740         750         760
             *   *   *   *   *   *   *   *   *
        GAT GCT GAT AAT GAC AAC TGT ATG TGC AAA TGT GCC CTC ATG TTA ACA
        Asp Ala Asp Asn Asp Asn Cys Met Cys Lys Cys Ala Leu Met Leu Thr
        ––e ––e ––e Ang1 FIBRINOGEN-LIKE DOMAIN ––e ––e ––e ––e 770         780         790         800         810
            *   *   *   *   *   *   *   *   *   *
        GGA GGA TGG TGG TTT GAT GCT TGT GGC CCC TCC AAT CTA AAT GGA ATG
        Gly Gly Trp Trp Phe Asp Ala Cys Gly Pro Ser Asn Leu Asn Gly Met
        ––e ––e ––e Ang1 FIBRINOGEN-LIKE DOMAIN ––e ––e ––e ––e 820         830         840         850         860
             *   *   *   *   *   *   *   *   *
        TTC TAT ACT GCG GGA CAA AAC CAT GGA AAA CTG AAT GGG ATA AAG TGG
        Phe Tyr Thr Ala Gly Gln Asn His Gly Lys Leu Asn Gly Ile Lys Trp
        ––e ––e ––e Ang1 FIBRINOGEN-LIKE DOMAIN ––e ––e ––e ––e 870         880         890         900         910
              *   *   *   *   *   *   *   *   *   *
        CAC TAC TTC AAA GGG CCC AGT TAC TCC TTA CGT TCC ACA ACT ATG ATG
        His Tyr Phe Lys Gly Pro Ser Tyr Ser Leu Arg Ser Thr Thr Met Met
        ––e ––e ––e Ang1 FIBRINOGEN-LIKE DOMAIN ––e ––e ––e ––e 920         930
                *   *   *   *
        ATT CGA CCT TTA GAT TTT TGA
        Ile Arg Pro Leu Asp Phe  *
        ––e – e ––e ––e ––e >
```

FIG. 5A

COMP-human Ang1

```
              10          20          30          40
         *    *     *     *     *     *     *     *     *
    ATG AAG ACG ATC ATC GCC CTG AGC TAC ATC TTC TGC CTG GTA TTC GCC
    Met Lys Thr Ile Ile Ala Leu Ser Tyr Ile Phe Cys Leu Val Phe Ala
    <—a —a —a HEMAGGLUTININ SIGNAL SEQUENCE—a —a —a —a>

50          60          70          80          90
     *    *     *     *     *     *     *     *     *     *
    GAC TAC AAG GAC GAT GAT GAC AAG GGG ATC TTA GAC CTA GCC CCA CAG
    Asp Tyr Lys Asp Asp Asp Asp Lys Gly Ile Leu Asp Leu Ala Pro Gln
    <—b—b —b FLAG TAG —b—>  # # # # #  <—c —c —c —c 100         110         120         130         140
      *    *     *     *     *     *     *     *     *
    ATG CTT CGA GAA CTC CAG GAG ACT AAT GCG GCG CTG CAA GAC GTG AGA
    Met Leu Arg Glu Leu Gln Glu Thr Asn Ala Ala Leu Gln Asp Val Arg
    —c —c —c —c —c COMP CC DOMAIN —c —c —c —c —c 150         160         170         180         190
      *    *     *     *     *     *     *     *     *     *
    GAG CTC TTG CGA CAG CAG GTC AAG GAG ATC ACC TTC CTG AAG AAT ACG
    Glu Leu Leu Arg Gln Gln Val Lys Glu Ile Thr Phe Leu Lys Asn Thr
    —c —c —c —c —c COMP CC DOMAIN —c —c —c —c —c 200         210         220         230         240
      *    *     *     *     *     *     *     *     *     *
    GTG ATG GAA TGT GAC GCT TGC GGA GGA TCC CTT GTC AAT CTT TGC ACT
    Val Met Glu Cys Asp Ala Cys Gly Gly Ser Leu Val Asn Leu Cys Thr
    —c —c COMP CC DOMAIN —c>  # # #  <—d —d —d —d —

250         260         270         280         290
      *    *     *     *     *     *     *     *     *
    AAA GAA GGT GTT TTA CTA AAG GGA GGA AAA AGA GAG GAA GAG AAA CCA
    Lys Glu Gly Val Leu Leu Lys Gly Gly Lys Arg Glu Glu Glu Lys Pro
    —d —d —d Ang1 LINKER REGION —d —d —d —d —d 300         310         320         330         340
      *    *     *     *     *     *     *     *     *     *
    TTT AGA GAC TGT GCA GAT GTA TAT CAA GCT GGT TTT AAT AAA AGT GGA
    Phe Arg Asp Cys Ala Asp Val Tyr Gln Ala Gly Phe Asn Lys Ser Gly
    —>X—e —e —e Ang1 FIBRINOGEN-LIKE DOMAIN —e —e —e —
```

FIG. 5B

```
          350       360       370       380
           *    *    *    *    *    *    *    *    *
         ATC TAC ACT ATT TAT ATT AAT AAT ATG CCA GAA CCC AAA AAG GTG TTT
         Ile Tyr Thr Ile Tyr Ile Asn Asn Met Pro Glu Pro Lys Lys Val Phe
         ――e ――e ――e ――e Ang1 FIBRINOGEN-LIKE DOMAIN ――e ――e ――e ―

390       400       410       420       430
       *    *    *    *    *    *    *    *    *    *
     TGC AAT ATG GAT GTC AAT GGG GGA GGT TGG ACT GTA ATA CAA CAT CGT
     Cys Asn Met Asp Val Asn Gly Gly Gly Trp Thr Val Ile Gln His Arg
     ――e ――e ――e ――e Ang1 FIBRINOGEN-LIKE DOMAIN ――e ――e ――e ―

440       450       460       470       480
       *    *    *    *    *    *    *    *    *    *
     GAA GAT GGA AGT CTA GAT TTC CAA AGA GGC TGG AAG GAA TAT AAA ATG
     Glu Asp Gly Ser Leu Asp Phe Gln Arg Gly Trp Lys Glu Tyr Lys Met
     ――e ――e ――e ――e Ang1 FIBRINOGEN-LIKE DOMAIN ――e ――e ――e ―

490       500       510       520       530
       *    *    *    *    *    *    *    *    *
     GGT TTT GGA AAT CCC TCC GGT GAA TAT TGG CTG GGG AAT GAG TTT ATT
     Gly Phe Gly Asn Pro Ser Gly Glu Tyr Trp Leu Gly Asn Glu Phe Ile
     ――e ――e ――e ――e Ang1 FIBRINOGEN-LIKE DOMAIN ――e ――e ――e ―

540       550       560       570       580
       *    *    *    *    *    *    *    *    *    *
     TTT GCC ATT ACC AGT CAG AGG CAG TAC ATG CTA AGA ATT GAG TTA ATG
     Phe Ala Ile Thr Ser Gln Arg Gln Tyr Met Leu Arg Ile Glu Leu Met
     ――e ――e ――e ――e Ang1 FIBRINOGEN-LIKE DOMAIN ――e ――e ――e ―

590       600       610       620
       *    *    *    *    *    *    *    *    *
     GAC TGG GAA GGG AAC CGA GCC TAT TCA CAG TAT GAC AGA TTC CAC ATA
     Asp Trp Glu Gly Asn Arg Ala Tyr Ser Gln Tyr Asp Arg Phe His Ile
     ――e ――e ――e ――e Ang1 FIBRINOGEN-LIKE DOMAIN ――e ――e ――e ―

630       640       650       660       670
       *    *    *    *    *    *    *    *    *    *
     GGA AAT GAA AAG CAA AAC TAT AGG TTG TAT TTA AAA GGT CAC ACT GGG
     Gly Asn Glu Lys Gln Asn Tyr Arg Leu Tyr Leu Lys Gly His Thr Gly
     ――e ――e ――e ――e Ang1 FIBRINOGEN-LIKE DOMAIN ――e ――e ――e ―

680       690       700       710       720
       *    *    *    *    *    *    *    *    *    *
     ACA GCA GGA AAA CAG AGC AGC CTG ATC TTA CAC GGT GCT GAT TTC AGC
     Thr Ala Gly Lys Gln Ser Ser Leu Ile Leu his Gly Ala Asp Phe Ser
     ――e ――e ――e ――e Ang1 FIBRINOGEN-LIKE DOMAIN ――e ――e ――e ―
```

FIG. 5C

```
          730         740         750         760         770
           *    *    *    *    *    *    *    *    *
        ACT AAA GAT GCT GAT AAT GAC AAC TGT ATG TGC AAA TGT GCC CTC ATG
        Thr Lys Asp Ala Asp Asn Asp Asn Cys Met Cys Lys Cys Ala Leu Met
        ——e ——e ——e ——e Ang1 FIBRINOGEN-LIKE DOMAIN ——e ——e ——e -

780         790         800         810         820
           *    *    *    *    *    *    *    *    *    *
        TTA ACA GGA GGA TGG TGG TTT GAT GCT TGT GGC CCC TCC AAT CTA AAT
        Leu Thr Gly Gly Trp Trp Phe Asp Ala Cys Gly Pro Ser Asn Leu Asn
        ——e ——e ——e ——e Ang1 FIBRINOGEN-LIKE DOMAIN ——e ——e ——e -

830         840         850         860         870
           *    *    *    *    *    *    *    *    *
        GGA ATG TTC TAT ACT GCG GGA CAA AAC CAT GGA AAA CTG AAT GGG ATA
        Gly Met Phe Tyr Thr Ala Gly Gln Asn His Gly Lys Leu Asn Gly Ile
        ——e ——e ——e ——e Ang1 FIBRINOGEN-LIKE DOMAIN ——e ——e ——e 880         890         900         910         920
           *    *    *    *    *    *    *    *    *    *
        AAG TGG CAC TAC TTC AAA GGG CCC AGT TAC TCC TTA CGT TCC ACA ACT
        Lys Trp His Tyr Phe Lys Gly Pro Ser Tyr Ser Leu Arg Ser Thr Thr
        ——e ——e ——e ——e Ang1 FIBRINOGEN-LIKE DOMAIN ——e ——e ——e -

930         940
           *    *    *    *    *
        ATG ATG ATT CGA CCT TTA GAT TTT TGA
        Met Met Ile Arg Pro Leu Asp Phe  *
        ——e ——e ——e ——e ——e ——e —>
```

Figure 13
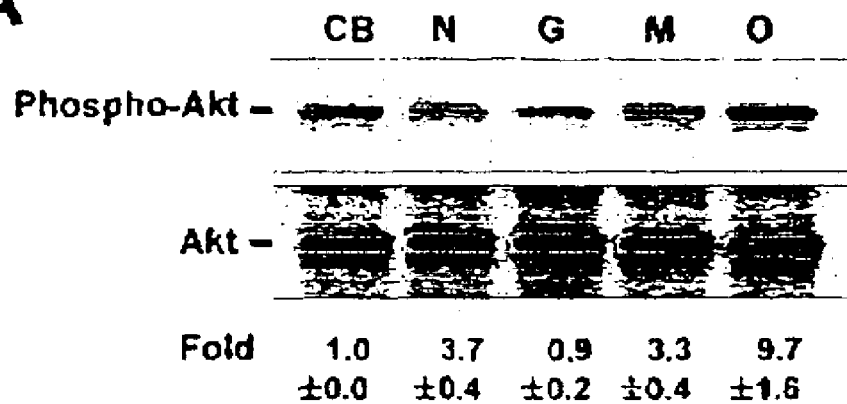
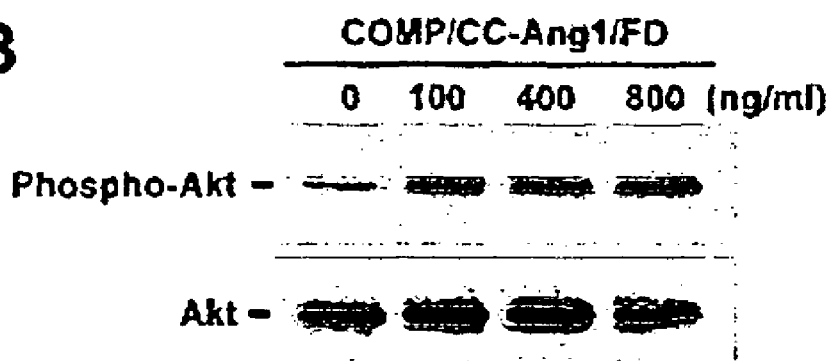
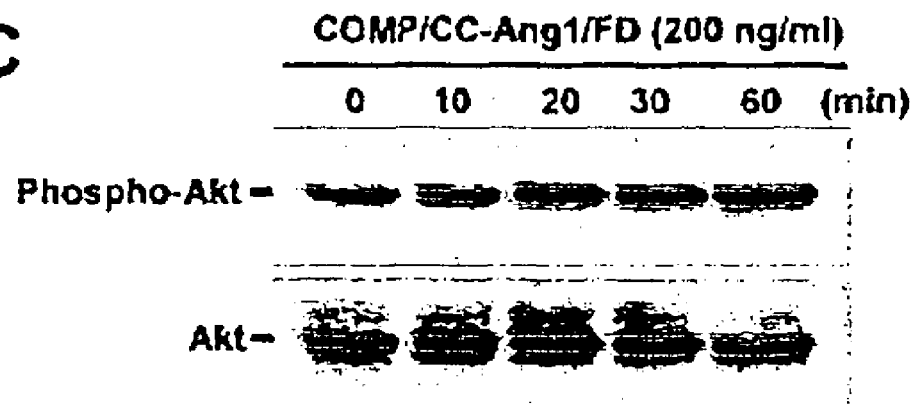

SEQUENCE LISTING

```
<160> NUMBER OF SEQ ID NOS: 30

<210> SEQ ID NO 1
<211> LENGTH: 786
<212> TYPE: DNA
<213> ORGANISM: Homo sapiens

<400> SEQUENCE: 1
atgtctgcac ttctgatcct agctcttgtt ggagctgcag ttgctgacta caaagacgat      60
gacgacaagc ttgtcaatct ttgcactaaa gaaggtgttt tactaaaggg aggaaaaaga     120
gaggaagaga aaccatttag agactgtgca gatgtatatc aagctggttt taataaaagt     180
ggaatctaca ctatttatat taataatatg ccagaaccca aaaaggtgtt ttgcaatatg     240
gatgtcaatg ggggaggttg gactgtaata caacatcgtg aagatggaag tctagatttc     300
```

-continued

```
caaagaggct ggaaggaata taaaatgggt tttggaaatc cctccggtga atattggctg    360
gggaatgagt ttatttttgc cattaccagt cagaggcagt acatgctaag aattgagtta    420
atggactggg aagggaaccg agcctattca cagtatgaca gattccacat aggaaatgaa    480
aagcaaaact ataggttgta tttaaaaggt cacactggga cagcaggaaa acagagcagc    540
ctgatcttac acggtgctga tttcagcact aaagatgctg ataatgacaa ctgtatgtgc    600
aaatgtgccc tcatgttaac aggaggatgg tggtttgatg cttgtggccc ctccaatcta    660 aatgaatgt tctatactgc gggacaaaac catggaaaac tgaatgggat aaagtggcac    720
tacttcaaag ggcccagtta ctccttacgt tccacaacta tgatgattcg acctttagat    780
ttttga                                                              786
```

```
<210> SEQ ID NO 2
<211> LENGTH: 260
<212> TYPE: PRT
<213> ORGANISM: Homo sapiens

<400> SEQUENCE: 2

Met Ser Ala Leu Leu Ile Ala Leu Leu Val Gly Ala Ala Val Ala Asp
1               5                   10                  15

Tyr Lys Asp Asp Asp Asp Lys Leu Val Asn Leu Cys Thr Lys Glu Gly
                20                  25                  30

Val Leu Leu Lys Gly Gly Lys Arg Glu Glu Glu Lys Pro Phe Arg Asp
            35                  40                  45

Cys Ala Asp Val Tyr Gln Ala Gly Phe Asn Lys Ser Gly Ile Tyr Thr
        50                  55                  60

Ile Tyr Ile Asn Asn Met Pro Glu Pro Lys Lys Val Phe Cys Asn Met
65                  70                  75                  80

Asp Val Asn Gly Gly Gly Trp Thr Val Ile Gln His Arg Glu Asp Gly
                85                  90                  95

Ser Leu Asp Phe Gln Arg Gly Trp Lys Glu Tyr Lys Met Gly Phe Gly
            100                 105                 110

Asn Pro Ser Gly Glu Tyr Trp Leu Gly Asn Glu Phe Ile Phe Ala Ile
        115                 120                 125

Tyr Ser Gln Arg Gln Tyr Met Leu Arg Ile Glu Leu Met Trp Glu Gly
    130                 135                 140

Asn Arg Ala Tyr Ser Gln Tyr Asp Arg Phe His Ile Gly Asn Glu Lys
145                 150                 155                 160

Gln Asn Tyr Arg Leu Tyr Leu Lys Gly His Thr Gly Tyr Ala Gly Lys
                165                 170                 175

Gln Ser Ser Leu Ile Leu His Gly Ala Asp Phe Ser Thr Lys Asp Ala
            180                 185                 190

Asp Asn Asp Asn Cys Met Cys Lys Cys Ala Leu Met Leu Thr Gly Gly
        195                 200                 205

Trp Trp Phe Asp Ala Cys Gly Pro Ser Asn Leu Asn Gly Met Phe Tyr
    210                 215                 220

Thr Ala Gly Gln Asn His Gly Lys Leu Asn Gly Ile Lys Trp His Tyr
225                 230                 235                 240

Phe Lys Gly Pro Ser Tyr Ser Leu Arg Ser Thr Thr Met Met Ile Arg
                245                 250                 255

Pro Leu Asp Phe
            260
```

<210> SEQ ID NO 3
<211> LENGTH: 897
<212> TYPE: DNA
<213> ORGANISM: Homo sapiens

<400> SEQUENCE: 3

```
atgaagacga tcatcgccct gagctacatc ttctgcctgg tattcgccga ctacaaggac      60
gatgatgaca gggggatctt aatgaaacag ctggaagaca agttgaaga actgctgtct     120
aaaaactacc acctggaaaa cgaagttgct cgtctgaaaa aactggttgg tgaaggatcc     180
cttgtcaatc tttgcactaa agaaggtgtt ttactaaagg gaggaaaaag agaggaagag     240
aaaccattta gagactgtgc agatgtatat caagctggtt ttaataaaag tggaatctac     300
actatttata ttaataatat gccagaaccc aaaaaggtgt tttgcaatat ggatgtcaat     360
gggggaggtt ggactgtaat acaacatcgt gaagatggaa gtctagattt ccaaagaggc     420
tggaaggaat ataaaatggg ttttggaaat ccctccggtg aatattggct ggggaatgag     480
tttattttg ccattaccag tcagaggcag tacatgctaa gaattgagtt aatggactgg     540
gaagggaacc gagcctattc acagtatgac agattccaca taggaaatga aaagcaaaac     600
tataggttgt atttaaaagg tcacactggg acagcaggaa acagagcag cctgatctta     660
cacggtgctg atttcagcac taaagatgct gataatgaca actgtatgtg caaatgtgcc     720
ctcatgttaa caggaggatg gtggtttgat gcttgtggcc cctccaatct aaatggaatg     780
ttctatactg cgggacaaaa ccatggaaaa ctgaatggga taaagtggca ctacttcaaa     840
gggcccagtt actccttacg ttccacaact atgatgattc gacctttaga tttttga     897
```

<210> SEQ ID NO 4
<211> LENGTH: 298
<212> TYPE: PRT
<213> ORGANISM: Homo sapiens

<400> SEQUENCE: 4

```
Met Lys Thr Ile Ile Ala Leu Ser Tyr Ile Phe Cys Leu Val Phe Ala
1               5                   10                  15

Asp Tyr Lys Asp Asp Asp Lys Gly Ile Leu Met Lys Gln Leu Glu
            20                  25                  30

Asp Lys Val Glu Glu Leu Leu Ser Lys Asn Tyr His Leu Glu Asn Glu
        35                  40                  45

Val Ala Arg Leu Lys Lys Leu Val Gly Glu Gly Ser Leu Val Asn Leu
    50                  55                  60

Cys Thr Lys Glu Gly Val Leu Leu Lys Gly Gly Lys Arg Glu Glu Glu
65                  70                  75                  80

Lys Pro Phe Arg Asp Cys Ala Asp Val Tyr Gln Ala Gly Phe Asn Lys
                85                  90                  95

Ser Gly Ile Tyr Thr Ile Tyr Ile Asn Asn Met Pro Glu Pro Lys Lys
            100                 105                 110

Val Phe Cys Asn Met Asp Val Asn Gly Gly Gly Trp Thr Val Ile Gln
        115                 120                 125

His Arg Glu Asp Gly Ser Leu Asp Phe Gln Arg Gly Trp Lys Glu Tyr
    130                 135                 140

Lys Met Gly Phe Gly Asn Pro Ser Gly Glu Tyr Trp Leu Gly Asn Glu
145                 150                 155                 160

Phe Ile Phe Ala Ile Tyr Ser Gln Arg Gln Tyr Met Leu Arg Ile Glu
                165                 170                 175

Leu Met Asp Trp Glu Gly Asn Arg Ala Tyr Ser Gln Tyr Asp Arg Phe
```

```
                    180                 185                 190
His Ile Gly Asn Glu Lys Gln Asn Tyr Arg Leu Tyr Leu Lys Gly His
            195                 200                 205

Thr Gly Tyr Ala Gly Lys Gln Ser Ser Leu Ile Leu His Gly Ala Asp
    210                 215                 220

Phe Ser Thr Lys Asp Ala Asp Asn Asp Asn Cys Met Cys Lys Cys Ala
225                 230                 235                 240

Leu Met Leu Thr Gly Gly Trp Trp Phe Asp Ala Cys Gly Pro Ser Asn
                245                 250                 255

Leu Asn Gly Met Phe Tyr Thr Ala Gly Gln Asn His Gly Lys Leu Asn
            260                 265                 270

Gly Ile Lys Trp His Tyr Phe Lys Gly Pro Ser Tyr Ser Leu Arg Ser
        275                 280                 285

Thr Thr Met Met Ile Arg Pro Leu Asp Phe
    290                 295
```

<210> SEQ ID NO 5
<211> LENGTH: 933
<212> TYPE: DNA
<213> ORGANISM: Homo sapiens

<400> SEQUENCE: 5

```
atgaagacga tcatcgccct gagctacatc ttctgcctgg tattcgccga ctacaaggac      60
gatgatgaca aggggatctt agatgaagat ccgtgcgaat ccaaaagcat agtgaaattc     120
cagaccaaag tggaagaact gatcaacacc ctgcagcaga aactggaagc ggtggcgaaa     180
cgtatcgaag cgctggaaaa caaaatcatc ggatcccttg tcaatctttg cactaaagaa     240
ggtgttttac taaagggagg aaaaagagag aagagaaac catttagaga ctgtgcagat      300
gtatatcaag ctggttttaa taaagtgga atctacacta tttatattaa taatatgcca      360
gaacccaaaa aggtgttttg caatatggat gtcaatgggg gaggttggac tgtaatacaa     420
catcgtgaag atggaagtct agatttccaa agaggctgga ggaatataa aatgggtttt      480
ggaaatccct ccggtgaata ttggctgggg aatgagttta tttttgccat taccagtcag     540
aggcagtaca tgctaagaat tgagttaatg gactgggaag ggaaccgagc ctattcacag     600
tatgacagat ccacatagg aaatgaaaag caaaactata ggttgtattt aaaaggtcac     660
actgggacag caggaaaaca gagcagcctg atcttacacg gtgctgattt cagcactaaa     720
gatgctgata tgacaactg tatgtgcaaa tgtgccctca tgttaacagg aggatggtgg     780
tttgatgctt gtggcccctc caatctaaat ggaatgttct atactgcggg acaaaaccat     840
ggaaaactga atgggataaa gtggcactac ttcaaagggc ccagttactc cttacgttcc     900
acaactatga tgattcgacc tttagatttt tga                                  933
```

<210> SEQ ID NO 6
<211> LENGTH: 309
<212> TYPE: PRT
<213> ORGANISM: Homo sapiens

<400> SEQUENCE: 6

```
Met Lys Thr Ile Ile Leu Ser Tyr Ile Phe Cys Leu Val Phe Ala Asp
1               5                   10                  15

Tyr Lys Asp Asp Asp Asp Lys Gly Ile Leu Asp Glu Asp Pro Cys Glu
            20                  25                  30

Cys Lys Ser Ile Val Lys Phe Gln Thr Lys Val Glu Glu Leu Ile Asn
        35                  40                  45
```

```
Thr Leu Gln Gln Lys Leu Glu Ala Val Ala Lys Arg Ile Glu Ala Leu
 50                  55                  60
Glu Asn Lys Ile Ile Gly Ser Leu Val Asn Leu Cys Thr Lys Glu Gly
 65                  70                  75                  80
Val Leu Leu Lys Gly Gly Lys Arg Glu Glu Lys Pro Phe Arg Asp
                 85                  90                  95
Cys Ala Asp Val Tyr Gln Ala Gly Phe Asn Lys Ser Gly Ile Tyr Thr
                100                 105                 110
Ile Tyr Ile Asn Asn Met Pro Glu Pro Lys Lys Val Phe Cys Asn Met
            115                 120                 125
Asp Val Asn Gly Gly Gly Trp Thr Val Ile Gln His Arg Glu Asp Gly
    130                 135                 140
Ser Leu Asp Phe Gln Arg Gly Trp Lys Glu Tyr Lys Met Gly Phe Gly
145                 150                 155                 160
Asn Pro Ser Gly Glu Tyr Trp Leu Gly Asn Glu Phe Ile Phe Ala Ile
                165                 170                 175
Tyr Ser Gln Arg Gln Tyr Met Leu Arg Ile Glu Leu Met Asp Trp Glu
            180                 185                 190
Gly Asn Arg Ala Tyr Ser Gln Tyr Asp Arg Phe His Ile Gly Asn Glu
    195                 200                 205
Lys Gln Asn Tyr Arg Leu Tyr Leu Lys Gly His Thr Gly Thr Ala Gly
225                 230                 235                 240
Lys Gln Ser Ser Leu Ile Leu His Gly Ala Asp Phe Ser Thr Lys Asp
225                 230                 235                 240
Ala Asp Asn Asp Asn Cys Met Cys Lys Cys Ala Leu Met Leu Thr Gly
                245                 250                 255
Gly Trp Trp Phe Asp Ala Cys Gly Pro Ser Asn Leu Asn Gly Met Phe
            260                 265                 270
Tyr Thr Ala Gly Gln Asn His Gly Lys Leu Asn Gly Ile Lys Trp His
    275                 280                 285
Tyr Phe Lys Gly Pro Ser Tyr Ser Leu Arg Ser Thr Thr Met Met Ile
290                 295                 300
Arg Pro Leu Asp Phe
305

<210> SEQ ID NO 7
<211> LENGTH: 939
<212> TYPE: DNA
<213> ORGANISM: Homo sapiens

<400> SEQUENCE: 7
atgaagacga tcatcgccct gagctacatc ttctgcctgg tattcgccga ctacaaggac    60
gatgatgaca agggatcttt agacctagcc ccacagatgc ttcgagaact ccaggagact   120
aatgcggcgc tgcaagacgt gagagagctc ttgcgcacag aggtcaagga gatcaccttc   180
ctgaagaata cggtgatgga atgtgacgct tgcggaggat cccttgtcaa tctttgcact   240
aaagaaggtg ttttactaaa gggaggaaaa agagaggaag agaaaccatt tagagactgt   300
gcagatgtat atcaagctgg ttttaataaa agtggaatct acactattta tattaataat   360
atgccagaac ccaaaaaggt gttttgcaat atggatgtca atggggaggg ttggactgta   420
atacaacatc gtgaagatgg aagtctagat ttccaaagag gctggaagga atataaaatg   480
ggttttggaa atccctccgg tgaatattgg ctggggaatg agtttatttt tgccattacc   540
agtcagaggc agtacatgct aagaattgag ttaatggact gggaagggaa ccgagcctat   600
```

```
tcacagtatg acagattcca cataggaaat gaaaagcaaa actataggtt gtatttaaaa    660
ggtcacactg gacagcagg aaaacagagc agcctgatct tacacggtgc tgatttcagc    720
actaaagatg ctgataatga caactgtatg tgcaaatgtg ccctcatgtt aacaggagga    780
tggtggtttg atgcttgtgg cccctccaat ctaaatggaa tgttctatac tgcgggacaa    840
aaccatggaa aactgaatgg gataaagtgg cactacttca aagggcccag ttactcctta    900
cgttccacaa ctatgatgat tcgaccttta gattttga                            939
```

<210> SEQ ID NO 8
<211> LENGTH: 312
<212> TYPE: PRT
<213> ORGANISM: Homo sapiens

<400> SEQUENCE: 8

```
Met Lys Thr Ile Ile Ala Leu Ser Tyr Ile Phe Cys Leu Val Phe Ala
1               5                   10                  15

Asp Tyr Lys Asp Asp Asp Lys Gly Ile Leu Asp Leu Ala Pro Gln
            20                  25                  30

Met Leu Arg Glu Leu Gln Glu Thr Asn Ala Ala Leu Gln Asp Val Arg
        35                  40                  45

Glu Leu Leu Arg Gln Gln Val Lys Glu Ile Thr Phe Leu Lys Asn Thr
    50                  55                  60

Val Met Glu Cys Asp Ala Cys Gly Gly Ser Leu Val Asn Leu Cys Thr
65                  70                  75                  80

Lys Glu Gly Val Leu Leu Lys Gly Gly Lys Arg Glu Glu Glu Lys Pro
                85                  90                  95

Phe Arg Asp Cys Ala Asp Val Tyr Gln Ala Gly Phe Asn Lys Ser Gly
            100                 105                 110

Ile Tyr Thr Ile Tyr Ile Asn Asn Met Pro Glu Pro Lys Lys Val Phe
        115                 120                 125

Cys Asn Met Asp Val Asn Gly Gly Gly Trp Thr Val Ile Gln His Arg
    130                 135                 140

Glu Asp Gly Ser Leu Asp Phe Gln Arg Gly Trp Lys Glu Tyr Lys Met
145                 150                 155                 160

Gly Phe Gly Asn Pro Ser Gly Glu Tyr Trp Leu Gly Asn Glu Phe Ile
                165                 170                 175

Phe Ala Ile Tyr Ser Gln Arg Gln Tyr Met Leu Arg Ile Glu Leu Met
            180                 185                 190

Asp Trp Glu Gly Asn Arg Ala Tyr Ser Gln Tyr Asp Arg Phe His Ile
        195                 200                 205

Gly Asn Glu Lys Gln Asn Tyr Arg Leu Tyr Leu Lys Gly His Thr Gly
    210                 215                 220

Thr Ala Gly Lys Gln Ser Ser Leu Ile Leu His Gly Ala Asp Phe Ser
225                 230                 235                 240

Thr Lys Asp Ala Asp Asn Asp Asn Cys Met Cys Lys Cys Ala Leu Met
                245                 250                 255

Leu Thr Gly Gly Trp Trp Phe Asp Ala Cys Gly Pro Ser Asn Leu Asn
            260                 265                 270

Gly Met Phe Tyr Thr Ala Gly Gln Asn His Gly Lys Leu Asn Gly Ile
        275                 280                 285

Lys Trp His Tyr Phe Lys Gly Pro Ser Tyr Ser Leu Arg Ser Thr Thr
    290                 295                 300

Met Met Ile Arg Pro Leu Asp Phe
```

<210> SEQ ID NO 9
<211> LENGTH: 25
<212> TYPE: DNA
<213> ORGANISM: Artificial
<220> FEATURE:
<223> OTHER INFORMATION: Primer for human Ang 1

<400> SEQUENCE: 9
gtgcggattc acaatgacag ttttc                                          25

<210> SEQ ID NO 10
<211> LENGTH: 25
<212> TYPE: DNA
<213> ORGANISM: Artificial
<220> FEATURE:
<223> OTHER INFORMATION: Primer for human Ang 1

<400> SEQUENCE: 10
gtgcggcagt acaatgacag ttttc                                          25

<210> SEQ ID NO 11
<211> LENGTH: 25
<212> TYPE: DNA
<213> ORGANISM: Artificial
<220> FEATURE:
<223> OTHER INFORMATION: Primer for human Ang 1

<400> SEQUENCE: 11
gctttcagat atctaaaggt cgaat                                          25

<210> SEQ ID NO 12
<211> LENGTH: 25
<212> TYPE: DNA
<213> ORGANISM: Artificial
<220> FEATURE:
<223> OTHER INFORMATION: Primer for human Ang 1

<400> SEQUENCE: 12
gctttcaaaa atctaaaggt cgaat                                          25

<210> SEQ ID NO 13
<211> LENGTH: 23
<212> TYPE: DNA
<213> ORGANISM: Artificial
<220> FEATURE:
<223> OTHER INFORMATION: Primer for human Ang 1

<400> SEQUENCE: 13
cagaaaagct tgggagaaga tat                                            23

<210> SEQ ID NO 14
<211> LENGTH: 22
<212> TYPE: DNA
<213> ORGANISM: Artificial
<220> FEATURE:
<223> OTHER INFORMATION: Primer for human Ang 1

<400> SEQUENCE: 14
tagaaggcac agtcgaggct ga                                             22

<210> SEQ ID NO 15
<211> LENGTH: 29
<212> TYPE: DNA
<213> ORGANISM: Artificial

<220> FEATURE:
<223> OTHER INFORMATION: Primer for GCN4

<400> SEQUENCE: 15
cagatcttaa tgaaacagct ggaagacaa                              29

<210> SEQ ID NO 16
<211> LENGTH: 31
<212> TYPE: DNA
<213> ORGANISM: Artificial
<220> FEATURE:
<223> OTHER INFORMATION: Primer for GCN4

<400> SEQUENCE: 16
ttggatcctt caccaaccag tttttttcaga c                          31

<210> SEQ ID NO 17
<211> LENGTH: 30
<212> TYPE: DNA
<213> ORGANISM: Artificial
<220> FEATURE:
<223> OTHER INFORMATION: Primer for CMP

<400> SEQUENCE: 17
ccagatctta gaagaagatc cgtgcgaatg                             30

<210> SEQ ID NO 18
<211> LENGTH: 29
<212> TYPE: DNA
<213> ORGANISM: Artificial
<220> FEATURE:
<223> OTHER INFORMATION: Primer for CMP

<400> SEQUENCE: 18
aaggatccga tgattttgtt ttccagcgc                              29

<210> SEQ ID NO 19
<211> LENGTH: 30
<212> TYPE: DNA
<213> ORGANISM: Artificial
<220> FEATURE:
<223> OTHER INFORMATION: Primer for COMP

<400> SEQUENCE: 19
ccagatctta gacctagccc cacagatgct                             30

<210> SEQ ID NO 20
<211> LENGTH: 30
<212> TYPE: DNA
<213> ORGANISM: Artificial
<220> FEATURE:
<223> OTHER INFORMATION: Primer for COMP

<400> SEQUENCE: 20
ttggatcctc cgcaagcgtc acattccatc                             30

<210> SEQ ID NO 21
<211> LENGTH: 109
<212> TYPE: DNA
<213> ORGANISM: Artificial
<220> FEATURE:
<223> OTHER INFORMATION: Primer for SHG-FLAG

<400> SEQUENCE: 21
aagcttaagc ttgccaccat gaagacgatc atcgccctga gctacatctt ctgcctggta      60

-continued ttcgccgact acaaggacga tgatgacaag gggatccact agtctcgag      109

<210> SEQ ID NO 22
<211> LENGTH: 109
<212> TYPE: DNA
<213> ORGANISM: Artificial
<220> FEATURE:
<223> OTHER INFORMATION: Primer for SHG-FLAG

<400> SEQUENCE: 22
ctcgagacta gtggatcccc ttgtcatcat cgtccttgta gtcggcgaat accaggcaga      60
agatgtagct cagggcgatg atcgtcttca tggtggcaag cttaagctt      109

<210> SEQ ID NO 23
<211> LENGTH: 30
<212> TYPE: DNA
<213> ORGANISM: Artificial
<220> FEATURE:
<223> OTHER INFORMATION: Primer for A1LF

<400> SEQUENCE: 23
ttggatccct tgtcaatctt tgcactaaag      30

<210> SEQ ID NO 24
<211> LENGTH: 33
<212> TYPE: DNA
<213> ORGANISM: Artificial
<220> FEATURE:
<223> OTHER INFORMATION: Primer for A1LF

<400> SEQUENCE: 24
ttctcgagtc aaaaatctaa aggtcgaatc atc      33

<210> SEQ ID NO 25
<211> LENGTH: 14
<212> TYPE: PRT
<213> ORGANISM: Artificial
<220> FEATURE:
<223> OTHER INFORMATION: Preprotrypsin leader sequence for Native Ang 1

<400> SEQUENCE: 25

Met Ser Ala Leu Leu Ile Leu Ala Leu Val Gly Ala Ala Ala
1               5                   10

<210> SEQ ID NO 26
<211> LENGTH: 8
<212> TYPE: PRT
<213> ORGANISM: Artificial
<220> FEATURE:
<223> OTHER INFORMATION: FLAG tag sequence

<400> SEQUENCE: 26

Asp Tyr Lys Asp Asp Asp Asp Lys
1               5

<210> SEQ ID NO 27
<211> LENGTH: 16
<212> TYPE: PRT
<213> ORGANISM: Artificial
<220> FEATURE:
<223> OTHER INFORMATION: bridging sequence

<400> SEQUENCE: 27

Asp Ile Gln His Ser Gly Gly Arg Ser Ser Leu Glu Gly Pro Arg Phe
1               5                   10                  15

-continued

```
<210> SEQ ID NO 28
<211> LENGTH: 10
<212> TYPE: PRT
<213> ORGANISM: Artificial
<220> FEATURE:
<223> OTHER INFORMATION: Myc epitope

<400> SEQUENCE: 28

Glu Gln Lys Leu Ile Ser Glu Glu Asp Leu
1               5                   10

<210> SEQ ID NO 29
<211> LENGTH: 5
<212> TYPE: PRT
<213> ORGANISM: Artificial
<220> FEATURE:
<223> OTHER INFORMATION: short bridging sequence

<400> SEQUENCE: 29

Asn Met His Thr Gly
1               5

<210> SEQ ID NO 30
<211> LENGTH: 6
<212> TYPE: PRT
<213> ORGANISM: Artificial
<220> FEATURE:
<223> OTHER INFORMATION: His-Tag sequence

<400> SEQUENCE: 30

His His His His His His
1               5
```

CHIMERIC COMP-ANG1 MOLECULE

CROSS-REFERENCE To RELATED APPLICATIONS

This application claims the benefit of U.S. Provisional Application No. 60/382,541, filed May 21, 2002, which disclosure is herein incorporated by reference.

BACKGROUND OF THE INVENTION

1. Field of the Invention

The present invention provides for novel method for producing novel chimeric molecules that have enhanced biological activity, and easier production and purification processes as compared with the molecules in their native form. The invention also provides for nucleic acids useful for producing biologically active chimeric polypeptides, and the fusion polypeptides themselves.

2. Description of the Background

Transmembrane protein kinases serve as signaling receptors for a variety of polypeptide ligands, eliciting such diverse responses as cell survival, proliferation and differentiation from many cell types and tissues (van der Geer et al., 1994, Annu Rev Cell Biol. 10:251–337). Receptor tyrosine kinases (RTKs) have the ability to interact with different ligands and bring about various cellular responses. One type of RTK is tyrosine kinase with immunoglobulin and epidermal growth factor receptor homology domains (Tie), Tie2 (Dumont et al., 1993, Oncogene 8:1293–1301; Mustonen and Alitalo, 1995, J Cell Biol. 129:895–898). Tie2 is expressed predominantly on endothelial cells, hematopoietic cells, or their embryonic precursors, and it is required for normal vascular development (Sato et al., 1995, Nature 376:70–74). Functional disruption of Tie2 in transgenic mice results in embryonic lethality by day E9.5 to 10.5, with effects on the microvasculature resulting in reduced numbers of endothelial cells, and abnormalities of vascular morphogenesis and hematopoiesis (Sato et al., 1995, Nature 376:70–74). Thus, Tie2 is critical for angiogenesis and hematopoiesis during development.

Davis et al. discovered that Ang1 is the ligand for Tie2 (Davis el al., 1996, Cell 87:1161–1169; WO9611269) (FIG. 1). Ang1 contains 498 amino acids, including an amino-terminal secretory signal sequence (FIG. 1). Human and mouse Ang1 are 97.6% identical. The amino-terminal region, consisting of residues 100–280, is weakly related to myosin and its relatives, in the regions of these proteins where they are known to possess coiled-coil quaternary structure (FIG. 1). The second region, consisting of residues 280–498, has strong similarity to the carboxy-terminal domain of fibrinogen (FIG. 1). Ang1 is a multimer, held together by coiled-coil structures and disulfide crosslinks. Recombinant Ang1 is a 70-kDa (reduced condition) secreted glycoprotein that binds to the Tie2 receptor with a Kd of approximately 3.7 nM, and induces tyrosine phosphorylation of Tie2 in endothelial cells (Davis et al., 1996, Cell 87:1161–1169).

Angiopoietin-1 (Ang1) is a specific and critical growth factor for blood vessel formation (Davis et al., 1996, Cell 87:1161–1169; Yancopoulos et al., 2000, Nature 407:242–248). Recent studies indicate that Ang1 could be used for preventing vascular leakages, therapeutic vasculogenesis, and therapeutic endothelial cell survival (Thurston et al., 2000, Nat. Med. 6:460–463; Chae et al., 2000, Arterioscler. Thromb. Vasc. Biol. 20:2573–2578; Kwak et al., 2000, Circulation 101:2317–2324). However, Ang1 protein is not easily available, and generation of recombinant Ang1 is extremely difficult with current techniques. Multimerization of the coiled coil domains during production of the ligand hampered purification.

Complementary DNAs encoding angiopoietin-2 (Ang2) were isolated by low-stringency screening of a cDNA library by using Ang1 cDNA as a probe (Maisonpierre et al., 1997, Science 277:55–60). Ang2 contains 496 amino acids and has a secretory signal sequence. Human and mouse Ang2 are 85% identical and approximately 60% identical to Ang1. Like Ang1, Ang2 has an amino-terminal coiled-coil domain and a carboxy-terminal fibrinogen-like domain. Ang1 and Ang2 have similar binding affinities for Tie2. Ang2 acts as an antagonist of Tie2 through inhibition of Ang1—induced phosphorylation of Tie2 (Maisonpierre et al., 1997, Science 277:55–60). Mouse angiopoietin-3 (Ang3) and human angiopoietin-4 (Ang4) were identified through low stringency hybridization screening with Ang1 and Ang2 cDNAs (Valenzuela et al., 1999, Proc Natl Acad Sci. 96:1904–1909). Ang3 and Ang4 are probably interspecies orthologs. Ang4 phosphorylates Tie2, while Ang3 inhibits Ang1-induced phosphorylation of Tie2 (Valenzuela et al., 1999, Proc Natl Acad Sci. 96:1904–1909).

Multimeric form of Ang1 phosphorylates Tie2. In turn, phosphorylated Tie2 interacts cytoplasmically with Grb2, Grb7, Grb14, the protein tyrosine phosphatase Shp2, and the p85 subunit of phosphatidylinositol 3'-kinase (PI 3'-kinase) via their SH2 domains (Jones et al., 1999, J Biol Chem. 274:30896–30905). Association between p85 and Tie2 results in PI 3'-kinase activation and subsequent induction of the serine-threonine kinase Akt. (Kontos et al., 1998, Mol Cell Biol. 18:4131–4140). Ang1 induces endothelial cell survival through this PI 3'-kinase/Akt signaling pathway (Kim et al., 2000, Circ Res. 86:24–29). In addition, Ang1 induces endothelial cell sprouting through the activation of PI 3'-kinase and focal adhesion kinase (Kim et al., 2000, Circ Res. 86:952–959). Thus, Tie2, PI 3'-kinase, Akt, and focal adhesion kinase are crucial elements in the signal transduction pathway leading to survival and migration in endothelial cells. Phosphorylated Tie2 also interacts with Dok-R/Dok-2, leading to activation of Dok-R/Dok-2 (Jones and Dumont, 1998, 17:1097–1108). Phosphorylated Dok-R interacts with rasGAP, Nck, and Crk (Jones and Dumont, 1998, 17:1097–1108). These signaling molecules may be involved in cell migration and proliferation, organization of the cytoskeleton, and regulation of Ras signaling. Recently, it was shown that Dok-R/Dok-2 is responsible for recruiting Nck and p21-activating kinase (Pak/Pak1) to the activated receptor (Master et al., 2001, EMBO J. 20:5919–5928). Localization of this Dok-R-Nck-Pak complex to the activated Tie2 at the cellular membrane is coincident with activation of Pak kinase (Master et al., 2001, EMBO J. 20:5919–5928). This signal transduction pathway may be involved in Ang1-mediated migration in endothelial cells. Signal transducers and activators of transcription (STATs) were also found to be potential targets of Tie2 activation (Korpelainen et al., 1999, Oncogene, 18:1–8). Phosphorylated Tie2, in turn, activates STAT3 and STAT5 (Korpelainen et al., 1999, Oncogene, 18:1–8). Since STAT3 and/or STAT5 are known to be involved in the regulation of cell proliferation, differentiation, migration, and survival in many biological systems, it is possible that some of the Tie2 functions in endothelial cells may be controlled through STAT pathway.

It is known that the Tie2 receptor is expressed not only in endothelial cells but also in hematopoietic stem cells (HSCs), indicating another possible role of Ang1 and Tie2 in hematopoiesis (Iwama et al., 1993, Biochem Biophys Res Commun 195:301–309). In fact, Tie2 deficient mice show severely impaired hematopoiesis (Sato et al., 1995, Nature 376:70–74). And HSCs closely adhere to endothelial cells at several sites in the embryo. Furthermore, it has been found that HSCs produce Ang1, suggesting that HSCs can promote the migration of endothelial cells and establish a hematopoietic environment (Takakura et al., 2000, Cell 102:199–209).

Ang1*, made by Regeneron Pharmaceuticals, Inc., is a recombinant version of Ang1 that is easier to produce and purify (Maisonpierre et al., 1997, Science 277:55–60; (PCT WO 98/05779)). Ang1* contains a modified amino-terminus and mutated $Cys^{265}$. The biological activity of recombinant Ang1 and Ang1* is similar. However, some of the same problems are encountered in producing Ang1* because the size of Ang1* is too large for efficient recombinant generation.

Both native Ang1 and Ang1* require extensive, expensive and labor-intensive purification schemes that result in relatively poor yields of recombinant protein. The need for cost-effective, simple purification schemes for biologicals intended for clinical use cannot be over-emphasized.

U.S. Pat. No. 6,455,035 discloses a method of decreasing or inhibiting vascular permeability in a mammal by administering to the mammal a Tie-2 receptor activator. However, U.S. Pat. No. '035 also discloses that the coiled coil domain of Ang1 was deleted so that the multimerization of the coiled coil domains would not hamper ligand purification.

WO 00/37462 discloses a method of enhancing the biological activity of Ang1 through deletion of coiled-coil domain and insertion with Fc-portion of immunoglobulin for making a tetramer form of chimeric fusion Ang1 (Ang1-1FD-Fc-FD). However, WO 00/37462 discloses that Ang1-1FD-Fc-FD is equivalent to Ang1* in its ability to stimulate phosphorylation of the Tie2 receptor.

Therefore, there is a need in the art to make a modified ligand molecule that is soluble and easily produced, while having substantially similar or greater potency as the native molecule.

SUMMARY OF THE INVENTION

The claimed invention overcomes the above-mentioned problems, and provides for novel, biologically active, soluble forms of chimeric polypeptide ligands that bind to specific receptors on cells, including growth factors belonging to angiopoietin family. Such polypeptide ligands are useful in promoting or inhibiting a differential function and/or influencing the phenotype, such as growth, survival, contractility, migration, and/or proliferation, of receptor-bearing cells such as endothelial cells, hematopoietic stem cells, and endothelial precursor cells. The invention also provides for nucleic acids encoding such polypeptide ligands, and both prokaryotic and eukaryotic expression systems for producing such polypeptide ligands. According to the invention, soluble forms of the polypeptide ligands described herein may be used to promote or inhibit biological responses in receptor-expressing cells.

The present invention is directed to a coiled coil chimeric molecule comprising a coiled-coil domain linked to either a receptor binding domain of a ligand or a ligand binding domain of a receptor, which forms a biologically active multimer, and wherein the chimeric molecule in its non-multimeric form is not biologically active.

Without limiting the source or structure of the coiled coil domain of the invention in any way, in one aspect, the coiled coil domain includes those belonging to a protein belonging to matrix protein family, transcription factor family, growth factor family or secretory protein family. Furthermore, the coiled coil domain may be of a matrix protein, in particular, cartilage matrix protein or cartilage oligomeric matrix protein.

In the coiled coil chimeric molecule, the receptor binding domain may bind to a variety of receptors, and in particular, Tie2 or Tie1 receptor. In one aspect, the receptor binding domain may be a fibrinogen-like domain of angiopoietin-1, angiopoietin-2, angiopoietin-3 or angiopoietin-4.

In another aspect of the invention, the coiled coil chimeric molecule may be linked directly or indirectly to an extracellular domain of the receptor.

In the coiled coil chimeric molecule, the ligand binding domain may bind to angiopoietin-1, angiopoietin-2, angiopoietin-3 or angiopoietin-4. The ligand binding domain may comprise extracellular domain of Tie2 receptor or Tie1 receptor. The ligand may be an agonist or antagonist. And the ligand may be a cytokine, hormone or growth factor.

The ligand may be also an angiopoietin-related protein. In particular, the ligand may be angiopoietin-related protein-1 (Arp1), angiopoietin-related protein-2 (ARP2), hepatic fibrinogen/angiopoietin-related protein (HFARP). The ligand may be ephrin. In particular, the ligand may be EphrinA1, EphrinA2, EphrinB1, or EphrinB2. In another aspect of the invention, the ligand may be thrombospondin. In particular, the thrombospondin may be TSP-1 or TSP-2.

In yet another aspect of the invention, with respect to the chimeric molecule, the ligand may be VEGF, PDGF, EGF, erythropoietin, interleukin, RANKL, FGF or NGF. In particular, the ligand may be VEGF-A, VEGF-B, VEGF-C, VEGF-D, VEGF-E, PDGF-A, PDGF-B, PDGF-C or PDGF-D.

In still another aspect of the invention, in the coiled coil chimeric molecule discussed above, the ligand may be angiopoietin-1, angiopoietin-2, angiopoietin-3 or angiopoietin-4. In particular, the ligand may be angiopoietin-1.

The present invention is also directed to an isolated nucleic acid encoding a coiled coil chimeric molecule, which is discussed above. Further, the invention is directed to an expression vector that includes this nucleic acid. A host cell comprising the vector is also included within the purview of the invention.

The present invention also includes a soluble biologically active multimer comprising the coiled coil chimeric molecule discussed above. In particular, the multimer may be a homomer or a homomer. If the multimer is a heteromer, then it is preferred that the coiled coil domain be heterogeneous with respect to at least one specie. The multimer may be a dimer, trimer, tetramer, pentamer, hexamer, heptamer, octamer, nanomer or decamer and so on without limitation. Moreover, the multimer may comprise coiled coil domains, which form parallel or anti-parallel structure.

The present invention is also directed to a method of promoting cell growth comprising contacting a coiled coil chimeric molecule comprising a coiled-coil domain linked to a receptor binding domain of a ligand as described above, to a population of cells that express receptors that are specific for the ligand, wherein said ligand is an agonist for said receptor, and wherein a multimeric form of the coiled coil chimeric molecule interacts with the receptor, which results in cell growth promotion. In particular, in this method, without being limited to any particular cell type, the cells may be endothelial cells, hematopoietic cells or other cells that express each specific receptor.

In another aspect of the invention, the present invention is directed to a method of promoting cell proliferation comprising contacting a coiled coil chimeric molecule comprising a coiled-coil domain linked to a receptor binding domain of a ligand as described above, to a population of cells that express receptors that are specific for the ligand, wherein said ligand is an agonist for said receptor, and wherein a multimeric form of the coiled coil chimeric molecule interacts with the receptor, which results in cell proliferation. In particular, in this method, without being limited to any particular cell type, the cells may be endothelial cells, hematopoietic cells or other cells that express each specific receptor.

In yet another aspect of the invention, the present invention is directed to a method of decreasing or inhibiting cell proliferation comprising contacting a coiled coil chimeric molecule comprising a coiled-coil domain linked to a ligand binding domain of a receptor as described above, to a population of cells that express ligands that are specific for the receptor, wherein a multimeric form of the coiled coil chimeric molecule interacts with the ligand, which results in decrease or inhibition of cell proliferation. In particular, in this method, without being limited to any particular cell type, the cells may be endothelial cells, hematopoietic cells or other cells that express each specific receptor.

In yet another aspect of the invention, the present invention is directed to a method of decreasing or inhibiting ligand activity comprising contacting a coiled coil chimeric molecule comprising a coiled-coil domain linked to a ligand binding domain of a receptor as described above, to a sample comprising a ligand that is specific for the receptor, wherein a multimeric form of the coiled coil chimeric molecule binds the ligand, which results in a decrease or inhibition of ligand activity.

In still another aspect of the invention, the present invention is directed to a method of making a chimeric molecule comprising: (A) recombinantly combining a nucleic acid encoding a coiled-coil domain with a nucleic acid encoding either a receptor binding region of a ligand or a ligand binding region of a receptor to produce a chimeric gene construct; and (B) expressing the gene construct in a host cell to produce the chimeric molecule. These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIGS. 2A–2C show nucleic acid sequence (SEQ ID NO:1) and deduced amino acid sequence (SEQ ID NO:2) of Ang1/FD (fibrinogen-like domain of Ang1).

FIGS. 3A–3C show nucleic acid sequence (SEQ ID NO:3) and deduced amino acid sequence (SEQ ID NO:4) of GCN4/CC-Ang1/FD (coiled-coil domain of GCN4-Ang1/FD).

FIGS. 4A–4C show nucleic acid sequence (SEQ ID NO:5) and deduced amino acid sequence (SEQ ID NO:6) of CMP/CC-Ang1/FD (coiled-coil domain of CMP-Ang1/FD).

FIGS. 5A–5C show nucleic acid sequence (SEQ ID NO:7) and deduced amino acid sequence (SEQ ID NO:8) of COMP/CC-Ang1/FD (coiled-coil domain of COMP-Ang1/FD).

FIGS. 13A–13C show comparison of native Ang1, GCN4-Ang1/FD, CMP-Ang1/FD, or COMP-Ang1/FD in Akt (Ser473) phosphorylation assay in HUVECs. In each panel, upper band indicates that the Western blots were probed with anti-phospho-Akt (Ser473) antibody. Lower band shows the blot that was reprobed with anti-Akt antibody to verify equal loading of protein in each lane. (A) HUVECs were incubated with control buffer (CB), and 200 ng of native Ang1 (N), GCN4Ang1/FD (G), CMP-Ang1/FD (M), or COMP-Ang1/FD (O) for 15 min. (B) HUVECs were incubated with control buffer (CB) and indicated amount of COMP-Ang1/FD. (C) HUVECs were incubated with 200 ng of COMP-Ang1/FD for indicated times. After treatment, cell lysates were harvested. Each lane contains 50 μg of total protein from the cell lysates. Results were similar in three independent experiments. Fold: Densitometric analyses are presented as the relative ratio of phospho-Akt (Ser472) to Akt. The relative ratio measured for control buffer was arbitrarily set at 1. Numbers represent the mean±S.D. from three experiments.

DETAILED DESCRIPTION OF THE INVENTION

Figure 1:
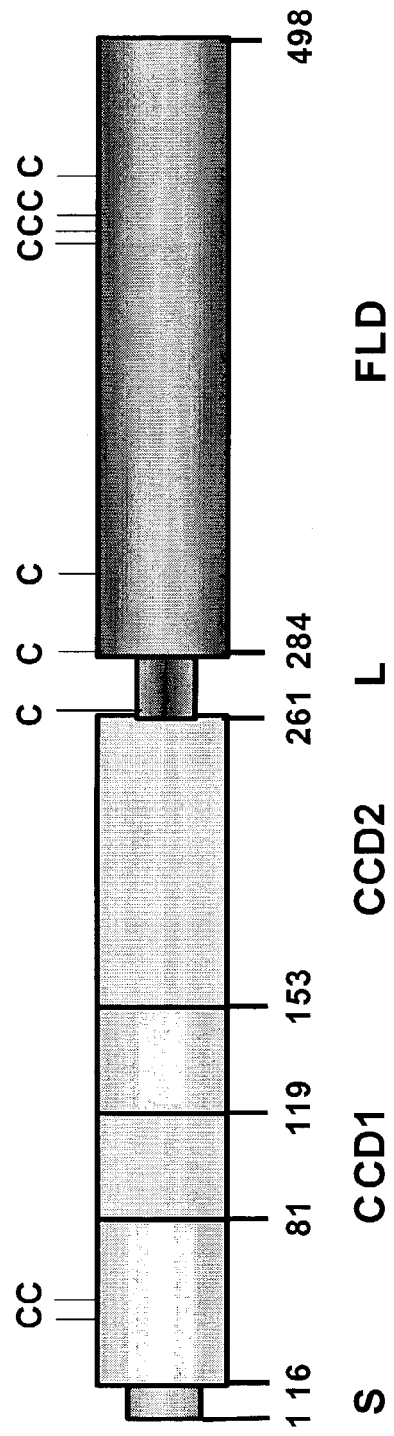
FIG. 1 shows a schematic structure of angiopoietin-1.

In the present application, "a" and "an" are used to refer to both single and a plurality of objects.

As described in greater detail below, applicants have discovered a method of using coiled-coil domains for "multimerizing" ligands, which enhances the biological activity of such ligands that, absent such multimerization, would have lower levels of biological activity. This method may be used to multimerize receptor binding domains from any ligand that has improved affinity and/or increased activity (i.e. signaling ability) when they were multimerized as compared to the non-multimerized form of the ligand.

The present invention also provides for methods of using coiled-coil domains for "multimerizing" soluble receptors, which functions to make otherwise inactive soluble receptors biologically active, or which enhances the biological and binding activity of receptors that, absent such multimerization, would have lower levels of biological and binding activity. This method may be used to multimerize ligand binding domains using any receptor, which has improved affinity and/or increased activity (i.e. binding) when they were multimerized as compared to the native form of the soluble receptor.

As used herein, "agonist" refers to a ligand that binds to a receptor, which activates the receptor and stimulates physiologic activity. For instance, Ang1 is considered to be an agonist of Tie2 receptor.

As used herein, "antagonist" refers to a ligand that tends to nullify the action of another ligand, as a ligand that binds to a cell receptor without eliciting a biological response.

As used herein, "biologically active" with regard to the ligand of the present invention refers to the ability of a molecule to specifically bind to and signal through a native receptor, e.g. a native Tie2 receptor, or to block the ability of a native Tie receptor (e.g. Tie2) to participate in signal transduction. Thus, the (native and variant) ligands of the present invention include agonists and antagonists of a native receptor, e.g. Tie2 receptor. Preferred biological activities of the ligands of the present invention include the ability to induce or inhibit vascularization. The ability to induce vascularization will be useful for the treatment of biological conditions and diseases, where vascularization is desirable. On the other hand, the ability to inhibit or block vascularization may, for example, be useful in preventing or attenuating cell proliferation and tumor growth.

Preferred biological activities of the ligands of the present invention include the ability to inhibit vascular permeability. The ability to inhibit vascular permeability will be useful for treatment of medical conditions and diseases such as diabetic retinopathy, edema, and ascites. Preferred biological activities of the ligands of the present invention include the ability to maintain endothelial cell integrity (including preventing apoptosis). The ability to maintain endothelial cell integrity will be useful for treatment of medical conditions and diseases such as mannitol treatment, irradiation, and sepsis.

The biological activity of the chimeric receptor, which may be in soluble form, includes its ability to inhibit or competitively inhibit the ligand's activity by binding to its ligand. Thus, in this way, cell proliferation may be inhibited if the ligand is an agonist for cell proliferation. Alternatively, administration of chimeric receptor may act as an enhancer of cell proliferation if the ligand is an antagonist for cell proliferation.

It is also contemplated that chimeric ligand and chimeric receptor be labeled with a detectable label, such as radioisotope, fluorescent tag, enzymatic tag, or a chemiluminescent tag to determine ligand-receptor binding interaction. As such assay systems employing the chimeric molecule is also contemplated.

As used herein, "chimeric ligand", "chimeric receptor", "chimeric polypeptide" or "chimeric molecule" refers to the combination of coiled coil domain and a receptor binding domain or a ligand binding domain. The resultant chimeric polypeptide is capable of forming biologically active multimers, which are soluble. The coiled coil domain may be derived from any source, including any animal or mammalian protein, and in particular any human protein, and further includes those that are synthetically made. Moreover, the coiled coil domain and the ligand or receptor constructs may be from the same or different source. It is understood that the chimeric construct comprises the coiled coil domain and a receptor binding domain of a ligand or a ligand binding domain of a receptor, and further may include other components that may be included so long their inclusion does not interfere with the formation of a biologically active multimer that has improved solubility, ease of recombinant production of the chimeric polypeptide and substantially similar or greater potency as the native ligand or native soluble receptor. For example, FLAG sequence may be included for ease of purification, provided its inclusion does not interfere with the function of the chimeric molecule. The FLAG sequence also may be removed if a humanized construct is desired.

As used herein, "fragments" or "functional derivatives" refers to biologically active amino acid sequence variants and fragments of the native ligands or receptors of the present invention, as well as covalent modifications, including derivatives obtained by reaction with organic derivatizing agents, post-translational modifications, derivatives with nonproteinaceous polymers, and immunoadhesins.

As used herein, "ligand binding domain" refers to the portion of the receptor that binds to the ligand and includes the minimal portion of the receptor that is necessary to bind its ligand.

As used herein, "linked" refers to direct or indirect connection between the multimerizing domain and the ligand or receptor. Both a direct fusion between these two domains or indirect fusion as by the domains being separated by a linker or an intervening domain or element are contemplated, so long as the activity of the chimeric fusion is present.

As used herein, "multimer" or "multimeric" refers to the joining of the multimerizing agent such as the coiled coil domain to each other to form a dimer, trimer, tetramer, pentamer, hexamer, heptamer, octamer, nanomer, decamer and so on, which may be in a parallel or anti-parallel form, through intramolecular or intermolecular bonds.

As used herein, "receptor binding domain" refers to the portion of the ligand that binds to the receptor and includes the minimal portion of the ligand that is necessary to bind its receptor. The present invention is based on the discovery that a multimerizing agent, such as a coiled coil domain, which was previously perceived as a source of hindrance for isolating recombinant proteins containing them, has been found to provide advantageous features of easy recombinant protein expression and purification, greater solubility and greater or substantially equal potency compared with the native protein containing the coiled coil domain.

The present invention includes a multimer forming domain. In particular, coiled coil domain is exemplified. The coiled coil domain may be any amino acid sequence that forms a coiled coil structure. While the exemplified coiled coil domains herein are those cloned from a variety of proteins, it is understood that various mutations and derivatization are encompassed by the invention, so long as the resultant coiled coil domain is recognized by a person of skill in the art as a coiled coil structure and the coiled coil domain containing chimera is capable of forming a multimer, is easily soluble, and is able to provide similar or greater potency with respect to the native ligand or receptor.

It is further understood that in certain situations, in linking together the multimerzing domain with either the receptor binding domain of the ligand or ligand binding domain of the receptor, the multimerizing domain and the binding domain may be from the same protein, or they may be from different proteins. For instance, Ang1 coiled coil domain may be linked to its own fibrinogen-like domain in a more efficiently manner. Or, a cartilage oligomeric matrix protein (COMP) could be linked to the Ang1 fibrinogen-like domain.

Coiled Coil

The α-helical coiled coil is probably the most widespread subunit oligomerization motif found in proteins. Accordingly, coiled coils fulfill a variety of different functions. In several families of transcriptional activators, for example, short leucine zippers play an important role in positioning the DNA-binding regions on the DNA (Ellenberger et al., 1992, Cell 71:1223–1237). Coiled coils are also used to form oligomers of intermediate filament proteins. Coiled-coil proteins furthermore appear to play an important role in both vesicle and viral membrane fusion (Skehel and Wiley, 1998, Cell 95:871–874). In both cases hydrophobic sequences, embedded in the membranes to be fused, are located at the same end of the rod-shaped complex composed of a bundle of long α-helices. This molecular arrangement is believed to cause close membrane apposition as the complexes are assembled for membrane fusion.

The coiled coil is often used to control oligomerization. It is found in many types of proteins, including transcription factors such as, but not limited to GCN4, viral fusion peptides, SNARE complexes and certain tRNA synthetases, among others. Very long coiled coils are found in proteins such as tropomyosin, intermediate filaments and spindle-pole-body components.

Coiled coils involve a number of helices that are supercoiled around each other in a highly organized manner that associate in a parallel or an antiparallel orientation. Although dimers and trimers are the most common. The helices may be from the same or from different proteins.

The coiled-coil is formed by component helices coming together to bury their hydrophobic seams. As the hydrophobic seams twist around each helix, so the helices also twist to coil around each other, burying the hydrophobic seams and forming a supercoil. It is the characteristic interdigitation of side chains between neighbouring helices, known as knobs-into-holes packing, that defines the structure as a coiled coil. The helices do not have to run in the same direction for this type of interaction to occur, although parallel conformation is more common. Antiparallel conformation is very rare in trimers and unknown in pentamers, but more common in intramolecular dimers, where the two helices are often connected by a short loop.

In the extracellular space, the heterotrimeric coiled-coil protein laminin plays an important role in the formation of basement membranes. Other examples are the thrombospondins and cartilage oligomeric matrix protein (COMP) in which three (thrombospondins 1 and 2) or five (thrombospondins 3, 4 and COMP) chains are connected. The molecules have a flower bouquet-like appearance, and the reason for their oligomeric structure is probably the multivalent interaction of the C-terminal domains with cellular receptors.

GCN4

The yeast transcriptional activator GCN4 is 1 of over 30 identified eukaryotic proteins containing the basic region leucine zipper (bZIP) DNA-binding motif (Ellenberger et al., 1992, Cell 71:1223–1237). The bZIP dimer is a pair of continuous alpha helices that form a parallel coiled-coil over their carboxy-terminal 34 residues and gradually diverge toward their amino termini to pass through the major groove of the DNA binding site. The coiled-coil dimerization interface is oriented almost perpendicular to the DNA axis, giving the complex the appearance of the letter T. bZIP contains a 4–3 heptad repeat of hydrophobic and nonpolar residues that pack together in a parallel alpha-helical coiled-coil (Ellenberger et al., 1992, Cell 71:1223–1237). The stability of the dimer results from the side-by-side packing of leucines and nonpolar residues in positions a and d of the heptad repeat, as well as a limited number of intra- and interhelical salt bridges, shown in a crystal structure of the GCN4 leucine zipper peptide (Ellenberger et al., 1992, Cell 71:1223–1237).

Cartilage Matrix Protein (CMP)

CMP (matrilin-1) was isolated from bovine tracheal cartilage as a homotrimer of subunits of $M_r$ 52,000 (Paulsson and Heinegård, 1981, Biochem J. 197:367–375), where each subunit consists of a vWFA1 module, a single EGF domain, a vWFA2 module and a coiled coil domain spanning five heptads (Kiss et al., 1989, J. Biol. Chem. 264:8126–8134; Hauser and Paulsson, 1994, J. Biol. Chem. 269:25747–25753). Electron microscopy of purified CMP showed a bouquet-like trimer structure in which each subunit forms an ellipsoid emerging from a common point corresponding to the coiled coil (Hauser and Paulsson, 1994, J. Biol. Chem. 269:25747–25753). The coiled coil domain in matrilin-1 has been extensively studied. The trimeric structure is retained after complete reduction of interchain disulfide bonds under non-denaturing conditions (Hauser and Paulsson, 1994, J. Biol. Chem. 269:25747–25753).

Cartilage oligomeric matrix protein (COMP)

A non-collagenous glycoprotein, COMP, was first identified in cartilage (Hedbom et al., 1992, J. Biol. Chem. 267:6132–6136). The protein is a 524 kDa homopentamer of five subunits which consists of an N-terminal heptad repeat region (cc) followed by four epidermal growth factor (EGF)-like domains (EF), seven calcium-binding domains (T3) and a C-terminal globular domain (TC). According to this domain organization, COMP belongs to the family of thrombospondins. Heptad repeats $(abcdefg)_n$ with preferentially hydrophobic residues at positions a and d form—helical coiled-coil domains (Cohen and Parry, 1994, Science 263: 488–489). Recently, the recombinant five-stranded coiled-coil domain of COMP (COMPcc) was crystallized and its structure was solved at 0.2 nm resolution (Malashkevich et al., 1996, Science 274:761–765).

The present invention also provides for a nucleic acid encoding a fusion polypeptide wherein the fusion polypeptide comprises a first subunit comprising at least one copy of the receptor binding domain of a ligand, the first subunit being fused to the C-terminal end of a multimerizing component.

Alternatively, the present invention provides for a nucleic acid encoding a fusion polypeptide wherein the fusion polypeptide comprises a first subunit comprising at least one copy of the receptor binding domain of a ligand, the first subunit being fused to the N-terminal end of a multimerizing component. In particular, the multimerizing component may be the coiled coil domain.

The present invention also provides for a nucleic acid encoding a fusion polypeptide wherein the fusion polypeptide comprises a first subunit comprising at least one copy of the ligand binding domain of a receptor, the first subunit being fused to the C-terminal end of a multimerizing component.

Alternatively, the present invention provides for a nucleic acid encoding a fusion polypeptide wherein the fusion polypeptide comprises a first subunit comprising at least one copy of the ligand binding domain of a receptor, the first subunit being fused to the N-terminal end of a multimerizing component. In particular, the multimerizing component may be the coiled coil domain.

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS or CHO cell.

The present invention also provides for methods of producing the fusion polypeptides of the invention by growing cells of the host-vector system described herein, under conditions permitting production of the fusion polypeptide and recovering the fusion polypeptide so produced. The fusion polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The fusion polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, fusion polypeptide includes functionally equivalent molecules in which amino acid residues are substituted for residues within the sequence resulting in a silent or conservative change. For example, one or more amino acid residues within the sequence can be substituted by another amino acid of a similar polarity which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express the fusion polypeptides of the invention are genetically engineered to produce them by, for example, transfection, transduction, electropration, or microinjection techniques.

In addition, the present invention contemplates use of the fusion polypeptides described herein in tagged form.

Any of the methods known to one skilled in the art for the insertion of DNA fragments into a vector may be used to construct expression vectors encoding the fusion polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the fusion polypeptides of the invention may be regulated by a second nucleic acid sequence so that the fusion polypeptide is expressed in a host transformed with the recombinant DNA molecule. For example, expression of the fusion polypeptides described herein may be controlled by any promoter/enhancer element known in the art. Promoters which may be used to control expression of the fusion polypeptide include, but are not limited to the long terminal repeat as described in Squinto et al., (1991, Cell 65:1–20); the SV40 early promoter region (Bernoist and Chambon, 1981, Nature 290:304–310), the CMV promoter, the M-MuLV 5' terminal repeat the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al., 1987, Genes and Devel. 1:161–171), beta-globin gene control region which is active in myeloid cells (Mogram et al., 1985, Nature 315: 338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378).

Thus, according to the invention, expression vectors capable of being replicated in a bacterial or eukaryotic host comprising nucleic acids encoding a fusion polypeptide as described herein, and in particular modified angiopoietin, are used to transfect the host and thereby direct expression of such nucleic acid to produce fusion polypeptides which may then be recovered in biologically active form. As used herein, a biologically active form includes a form capable of binding to the relevant receptor and causing a differentiated function and/or influencing the phenotype of the cell expressing the receptor. Such biologically active forms would, for example, induce phosphorylation of the tyrosine kinase domain of Tie2 receptor, or stimulation of synthesis of cellular DNA.

Expression vectors containing the nucleic acid inserts can be identified by without limitation, at least three general approaches: (a) DNA—DNA hybridization, (b) presence or absence of "marker" gene functions, and (c) expression of inserted sequences. In the first approach, the presence of foreign nucleic acids inserted in an expression vector can be detected by DNA—DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The fusion polypeptide, in particular modified angiopoietin of the present invention, may be expressed in the host cells transiently, constitutively or permanently.

The invention herein further provides for the development of a fusion polypeptide as a therapeutic agent for the treatment of patients suffering from disorders involving cells, tissues or organs which express the Tie2 receptor. Such molecules may be used in a method of treatment of the human or animal body, or in a method of diagnosis.

Because Tie2 receptor has been identified in association with endothelial cells and, blocking of agonists of the receptor such as Ang-1 has been shown to prevent vascularization, applicants expect that Tie2 agonist fusion polypeptides of the invention may be useful for the induction of vascularization in diseases or disorders where such vascularization is indicated. Such diseases or disorders would include wound healing, ischemia and diabetes. The ligands may be tested in animal models and used therapeutically as described for other agents, such as vascular endothelial growth factor (VEGF), which is another endothelial cell-specific angiogenic factor.

U.S. Pat. No. 5,332,671, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired. See also European Patent Application 0 550 296 A2; Banai, et al., Circulation 89:2183–2189 (1994); Unger, et al. Am. J. Physiol. 266:H1588-H1595 (1994); and Lazarous, et al. Circulation 91:145–153 (1995). According to the invention, the agonist fusion polypeptides may be used alone or in combination with one or more additional pharmaceutically active compounds such as, for example, VEGF or basic fibroblast growth factor (bFGF).

Conversely, antagonists of the Tie2 receptor, such as Tie2 receptorbodies or Ang-2 as described in Example 9 in WO 96/31598, have been shown to prevent or attenuate vascularization in certain situations and in certain amounts. Similarly, Tie2 antagonist fusion polypeptides of the invention would also be useful for those purposes. These antagonists may be used alone or in combination with other compositions, such as anti-VEGF antibodies, that have been shown to be useful in treating conditions in which the therapeutic intent is to block angiogenesis.

In other embodiments, the Tie2 agonist fusion polypeptides of the invention described herein may be used as hematopoietic factors. A variety of hematopoietic factors and their receptors are involved in the proliferation and/or differentiation and/or migration of the various cells types contained within blood. Because Tie2 receptors are expressed in early hematopoietic cells, the Tie2 ligands are expected to play a comparable role in the proliferation or differentiation or migration of these cells. Thus, for example, Tie2 agonist fusion polypeptide compositions may be prepared, assayed, examined in in vitro and in vivo biological systems and used therapeutically as described in any of the following: U.S. Pat. No. 4,810,643; Lee, et al., Proc. Natl. Acad. Sci. USA 82:4360–4364 (1985); Wong, et al. Science, 228:810–814 (1985); Yokota, et al. Proc. Natl. Acad. Sci (USA) 81:1070 (1984); WO 9105795; and WO 95/19985.

Accordingly, the fusion polypeptides may be used to diagnose or treat conditions in which normal hematopoiesis is suppressed, including, but not limited to anemia, thrombocytopenia, leukopenia and granulocytopenia. In a preferred embodiment, the fusion polypeptides may be used to stimulate differentiation of blood cell precursors in situations where a patient has a disease, such as acquired immune deficiency syndrome (AIDS), which is associated with reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The fusion polypeptides of the present invention may be used alone, or in combination with other pharmaceutically active agents such as, for example, cytokines, neurotrophins, interleukins, etc. In a preferred embodiment, the fusion polypeptides may be used in conjunction with any of a number of factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF and so on.

In an alternative embodiment, Tie2 receptor antagonist fusion polypeptides are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the fusion polypeptides as described herein.

Effective doses useful for treating these or other diseases or disorders may be determined using methods known to one skilled in the art (see, for example, Fingl, et al., The Pharmacological Basis of Therapeutics, Goodman and Gilman, eds. Macmillan Publishing Co, New York, pp. 1–46 (1975). Pharmaceutical compositions for use according to the invention include the fusion polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a fusion polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the fusion polypeptides described herein, in a pharmacologically acceptable vehicle. The compositions may be administered systemically or locally. Any appropriate mode of administration known in the art may be used, incuding, but not limited to, intravenous, intrathecal, intraarterial, intranasal, oral, subcutaneous, intraperitoneal, or by local injection or surgical implant. Sustained release formulations are also provided for.

The present invention is not to be limited in scope by the specific embodiments described herein. Indeed, various modifications of the invention in addition to those described herein will become apparent to theose skilled in the art from the foregoing description and accompanying figures. Such modifications are intended to fall within the scope of the appended claims. The following examples are offered by way of illustration of the present invention, and not by way of limitation.

EXAMPLES

Example 1

Multimerization of Ang1 for Tie2 Phosphorylation

To determine the role of the amino-terminal region in relation to Tie2 receptor, truncated Ang1 that contains only fibrinogen-like domain (amino acids 284–498) (Ang1/FD) was generated. Recombinant Ang1/FD was a ~34 kDa secreted monomer, while recombinantly produced native Ang1 was a multimer (data not shown). Interestingly, the monomeric Ang1/FD did not bind to soluble Tie2, nor did it phosphorylate Tie2. In contrast, native Ang1 bound to Tie2 and also phosphorylated it. Thus, it appeared that both the amino terminus and multimerization of Ang1 could be necessary for Tie2 binding and activation.

To determine the role of $Cys^{41}$, $Cys^{54}$ and $Cys^{265}$ in Ang1 multimerization, the amino acid 17–80 region was deleted (Ang1-D1) and $Cys^{265}$ was substituted with $Ser^{265}$ (Ang1S265). SDS-PAGE gel analysis revealed that recombinant Ang1-D1 was present in as a trimer and Ang1S265 took on several types of multimeric forms including dimer and monomer. These data suggest that $CyS^{41}$, $Cys^{54}$ and $Cys^{265}$ of Ang1 participate in inter- and extra-molecular disulfide bond formation to form Ang1 multimers.

To determine the role of coiled-coil domains for Ang1 multimerization, we gradually deleted amino-terminal portion of Ang1. SDS-PAGE gel analysis revealed that deletion of amino acids 17–119 (Ang1-D2), amino acids 17–153 (Ang1-D3), and amino acids 17–212 (Ang1-D4) resulted in the formation of trimer, and dimer. In vitro binding assay with soluble Tie2-Fc showed that Ang1-D2, Ang1-D3, and Ang1-D4 bound to Tie2. Interestingly, trimeric Ang1-induced Tie2 phosphorylation was greater than dimeric Ang1-induced Tie2 phosphorylation. The data suggest that higher-order multimers induce greater level of Tie2 phosphorylation. In addition, the second coiled-coil domain (amino acids 153–261) and linker domain appear to be significant factors for creating higher-order multimerization. Moreover, multimerization of Ang1 is essential for Tie2 binding.

Example 2

Generation of Gene Constructs for Native Ang1

The full cDNA of human Ang1 was amplified from human adult heart cDNA library (Clontech) by PCR for 30 cycles at an annealing temperature of 52° C. using sense (5'-GTGCGGATTCACAATGACAGTTTTC-3' (SEQ ID NO:9), including BamHI restriction enzyme site; original 5'-GTGCGGCAGTACAATGACAGTTTTC-3' (SEQ ID NO:10)) and antisense primers (5'-GCTTTCAGATATCTA AAGGTCGAAT-3' (SEQ ID NO:11), including EcoRV restriction enzyme site; original 5'-GCTTTCAAAAAT CTAAAGGTCGAAT-3' (SEQ ID NO:12)). The amplified DNA was cloned into the pCR-Blunt vector (Invitrogen) and sequence determined.

Thus obtained human Ang1 cDNA was re-subcloned into a CMV promoter-driven mammalian cell expression vector, pcDNA3.1/Myc-His (Invitrogen), which has a DNA fragment (63 bp) encoding c-myc and a 6×His tag at the 3'-terminus of the coding region as an open reading frame (CMV-Ang1-M-H).

To generate the recombinant Ang1 that has an N-terminal FLAG tag, PCR was performed on CMV-Ang1-M-H for 25 cycles at an annealing temperature of 60° C. using sense primer (5'-CAGAAAAGCTTGGGAGAAGATAT-3' (SEQ ID NO:13)) and antisense primer (5'-TAGAAGGCA-CAGTCGAGGCTGA-3' (SEQ ID NO:14)). The PCR products were subcloned into cloning vector pCR2.1 (Invitrogen) and sequenced. The insert was cut with HindIII and PmeI, then subcloned into HindIII and EcoRV sites in pFLAG-CMVI (Sigma). This vector was named 'native Ang1'.

Example 3

Generation of Gene Constructs for Chimeric Coiled-Coil Containing Ang1

In order to generate multimeric but smaller molecular weight Ang1, the amino-terminal portion of Ang1 (261 amino-acid) was replaced with the short coiled-coil domain of yeast transcriptional activator GCN4, cartilage matrix protein (CMP; matrilin), and cartilage oligomeric matix protein (COMP). The coiled-coil domain of GCN4 is 31-amino acids and forms a parallel dimer. The coiled-coil domain of CMP is 43-amino acids and forms a parallel trimer. The coiled-coil domain of COMP is 45-amino acids and forms a parallel pentamer. Dr. Richard A. Kammerer (Department of Structural Biology, University of Basel) provided cDNA encoding coiled-coil domain of yeast GCN4, chicken CMP, and rat COMP.

PCR primers for coiled-coil domain of GCN4, CMP and COMP including BglII and BamH1 restriction enzyme sites were designed.

```
GCN4 BglII, Sense primer:     5'-cagatcttaatgaaacagctggaagacaa-3'.      (SEQ ID NO:15)

GCN4 BamHI, Antisense primer: 5'-ttggatccttcaccaaccagttttttcagac-3'.   (SEQ ID NO:16)

CMP BglII, Sense primer:      5'-ccagatcttagaagaagatccgtgcgaatg-3'.    (SEQ ID NO:17)

CMP BamHI, Antisense primer:  5'-aaggatccgatgattttgttttccagcgc-3'.     (SEQ ID NO:18)

COMP BglII, Sense primer:     5'-ccagatcttagacctagcccacagatgct-3'.     (SEQ ID NO:19)

COMP BamHI, Antisense primer: 5'-ttggatcctccgcaagcgtcacattccatc-3'.    (SEQ ID NO:20)
```

PCR was performed for 30 cycles at an annealing temperature of 52° C. The PCR products were subcloned into cloning vector pZErO-2 (InVitrogen) and sequenced. It was named 'pZErO-2CCD'.

In order to generate the secretion signal sequence of hemagglutinin and FLAG including HindIII, BamH1 and XhoI restriction enzyme sites, the following sense and antisense oligonucleotides were synthesized.

SHG-FLAG HindIII-BamHI-XhoI (HBX) Sense primer:

```
                                                    (SEQ ID NO:21)
5'AAGCTTAAGCTTGCCACCATGAAGACGATCATCGCCCTGAGCTACATC

TTCTGCCTGGTATTCGCCGACTACAAGGACGATGATGACAAGGGGATCCAC

TAGTCTCGAG-3'.
```

SHG-FLAG XhoI-BamH1-HindIII (XBH) Antisense primer:

(SEQ ID NO:22)
5'<u>CTCGAG</u>ACTAGTGGATCCCCTTGTCATCATCGTCCTTGTAGTCGGCGA

ATACCAGGCAGAAGATGTAGCTCAGGGCGATGATCGTCTTCATGGTGGC

<u>AAGCTT</u>AAGCTT-3'.

Sense and antisense nucleotides were annealed. The annealed reactants were ligated into the HindIII and XhoI sites of the mammalian cell expression vector, pCDNA3.1 (InVitrogen). This vector was named 'pCDNA-Signal-FLAG', which was incubated with BglII and BamH1. The released PCR fragment was inserted into BamH1 digested pCDNA-Signal-FLAG. This vector was named 'pCDNA-Signal-FLAG-CC'.

PCR primers for the linker and fibrinogen domain of Ang1 (from Leu261 to termination) including BamH1 and XhoI restriction enzyme sites were designed.

A1LF BamH1, Sense primer: 5'-ttg<u>gatcc</u>cttgtcaatctttgcac taaag -3' (SEQ ID NO:23).

A1LF Xho1, Antisense primer: 5'tt<u>ctcgag</u>tcaaaaatctaaagg tcgaatcatc-3' (SEQ ID NO:24).

Figure 6:
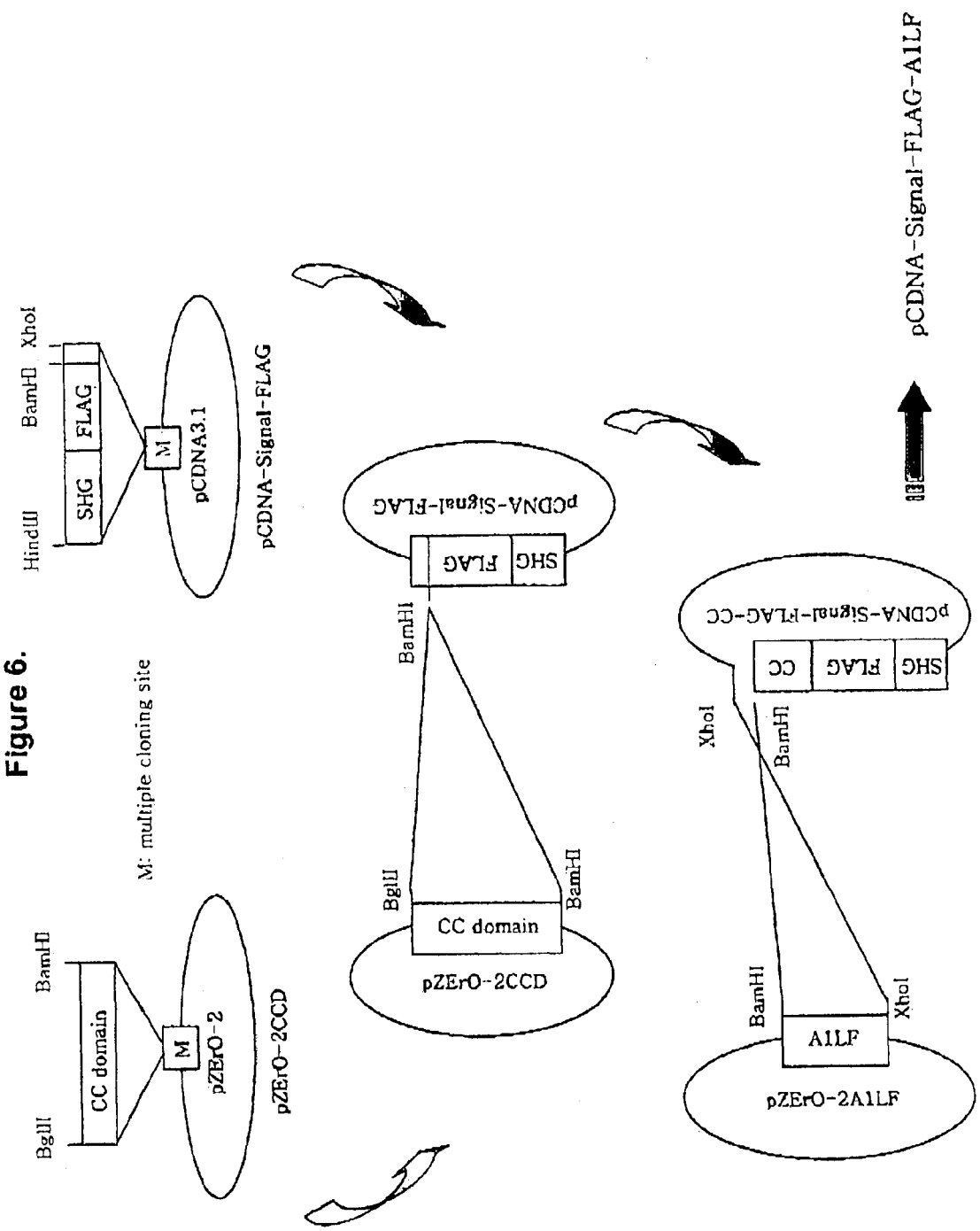
FIG. 6 shows a schematic diagram for generation of gene constructs for multimeric chimeric-Ang1. "M" stands for multiple cloning site.

PCR was performed for 30 cycles at an annealing temperature of 52° C. The PCR products were subcloned into cloning vector pZErO-2 (InVitrogen) and sequenced. It was named 'pZErO-2A1LF', which was incubated with BamHI and Xho1. The released PCR fragment was inserted into BamH1 and XhoI digested pCDNA-Signal-FLAG-CC. This vector was named 'pCDNA-Signal-FLAG-CC-A1LF'. FIG. 6 shows a schematic diagram for generating gene constructs for the multimeric chimeric-Ang1.

Figure 7:
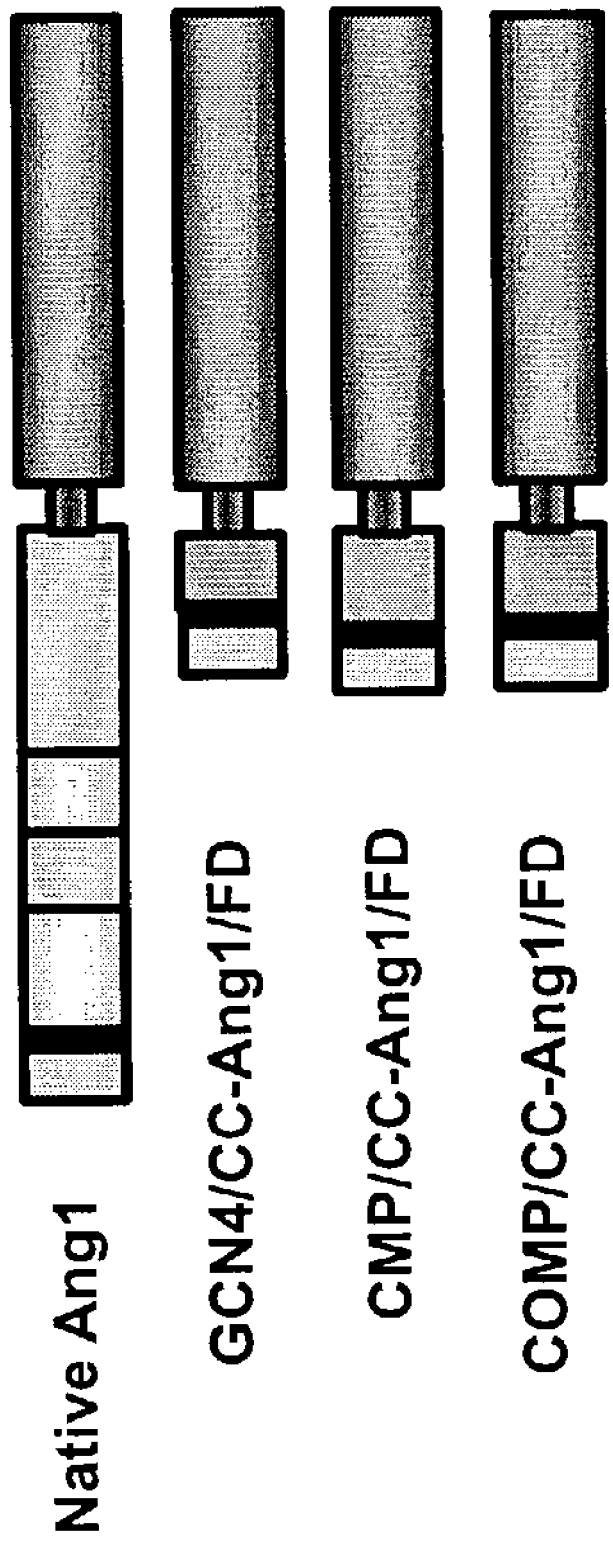
FIG. 7 shows a schematic diagram of native Ang1, GCN4-Ang1/FD, CMP-Ang1/FD, and COMP-Ang1/FD.

As described supra, four gene constructs were made and confirmed by sequence analysis. See FIG. 7.

(1) pCDNA-Signal-FLAG-human Ang1 (native Ang1).

(2) pCDNA-Signal-FLAG-coiled-coil domain of GCN4-fibrinogen domain of Ang1 (GCN4/CC-Ang1/FD).

(3) pCDNA-Signal-FLAG-coiled-coil domain of CMP-fibrinogen domain of Ang1 (CMP/CC-Ang1/FD).

(4) pCDNA-Signal-FLAG-coiled-coil domain of COMP-fibrinogen domain of Ang1 (COMP/CC-Ang1/FD).

All of the above nucleic acid molecules were constructed by standard recombinant DNA techniques (See e.g., Molecular Cloning, A Laboratory Manual, Sambrook, et al., Cold Spring Harbor Laboratory, Cold Spring Harbor, N.Y.; Current Protocols in Molecular Biology (Eds. Ausubel, et al., Greene Publ. Assoc., Wiley-Interscience, NY), sequence-verified by standard techniques using an ABI PRISM 3100 Genetic Analyzer (Applied Biosystems, Foster City, Calif.) and Taq Dideoxy Terminator Cycle Sequencing Kit using BigDye Terminator Cycle Sequencing version 2.0 (Applied Biosystems, Inc., Foster City, Calif.), ABI 373A DNA sequencer and and subcloned into the mammalian expression vector pcDNA3.1 (Invitrogen, Inc.).

The bridging sequences described infra were introduced to provide convenient restriction sites and to give flexibility to the junctions between the domains, but there is no indication that there is a critical nature to these bridging sequences, though varying the length of the linker in some of these constructs led to some variation in the amount of protein produced.

Example 4

Construction Of Native Ang1

Native Ang1 consists of a preprotrypsin leader sequence (Met-Ser-Ala-Leu-Leu-Ile-Leu-Ala-Leu-Val-Gly-Ala-Ala-Ala (SEQ ID NO:25)) at its amino terminus to allow for secretion (bases 1–42), a FLAG tag sequence (Asp-Tyr-Lys-Asp-Asp-Asp-Asp-Lys (SEQ ID NO:26), bases 43–66), a bridging amino acid Leu (bases 67–69), the coding sequence of Ang1 (bases 70–1470), another bridging sequence consisting of the amino acids Asp-Ile-Gln-His-Ser-Gly-Gly-Arg-Ser-Ser-Leu-Glu-Gly-Pro-Arg-Phe (SEQ ID NO:27) (bases 1471–1518), and the Myc epitope (Glu-Gln-Lys-Leu-Ile-Ser-Glu-Glu-Asp-Leu (SEQ ID NO:28), bases 1519–1548), and a short bridging sequence consisting of amino acids Asn-Met-His-Thr-Gly (SEQ ID NO:29) (bases 1549–1563) followed by His-Tag (His-His-His-His-His-His (SEQ ID NO:30), bases 1564–1581).

Example 5

Construction of the GCN4/CC-Ang1FD

GCN4/CC-Ang1/FD consists of a hemagglutinin signal sequence at its amino terminus to allow for secretion (bases 1–48 of SEQ ID NO:3 (FIG. 3A), a FLAG tag sequence (bases 49–72 of SEQ ID NO:3 (FIG. 3A)), a short bridging sequence consisting of the amino acids Gly-Ile-Leu of SEQ ID NO:3 (FIG. 3A)), the coding sequence of GCN4 coiled-coil domain (bases 82–174 of SEQ ID NO:3 (FIG. 3A)), another bridging sequence of the amino acids Gly-Ser (bases 175–180 of SEQ ID NO:3 (FIG. 3A)), and the coding sequence for the linker region of Ang1 (bases 181–249 of SEQ ID NO:3 (FIG. 3A)) followed by fibrinogen domain of Ang1 (FD) (bases 250–897 of SEQ ID NO:3 (FIGS. 3A–3C)).

Example 6

Construction of the CMP/CC-ANG1/FD

CMP/CC-Ang1/FD consists of a hemagglutinin signal sequence at its amino terminus to allow for secretion (bases 1–48 of SEQ ID NO:5 (FIG. 4A)), a FLAG tag sequence (bases 49–72 of SEQ ID NO:5 (FIG. 4A)), a short bridging sequence consisting of the amino acids Gly-Ile-Leu (bases 73–81 of SEQ ID NO:5 (FIG. 4A)), the coding sequence of CMP coiled-coil domain (bases 82–210 of SEQ ID NO:5 (FIG. 4A)), another bridging sequence consisting of the amino acids Gly-Ser (bases 211–216 of SEQ ID NO:5 (FIG. 4A)), and the coding sequence for the linker region of Ang1 (bases 217–285 of SEQ ID NO:5 (FIG. 4A)) followed by fibrinogen domain of Ang1 (FD) (bases 286–933 of SEQ ID NO:5 (FIGS. 4A–4C)).

Example 7

Construction of the COMP/CC-ANG1/FD

COMP/CC-Ang1/FD consists of a hemagglutinin signal sequence at its amino terminus to allow for secretion (bases 1–48 of SEQ ID NO:7 (FIG. 5A)), a FLAG tag sequence (bases 49–72 of SEQ ID NO:7 (FIG. 5A)), a short bridging sequence consisting of the amino acids Gly-Ile-Leu (bases 73–81 of SEQ ID NO:7 (FIG. 5A)), the coding sequence of COMP coiled-coil domain (bases 82–221 of SEQ ID NO:7

(FIG. 5A)), another bridging sequence consisting of amino acids Gly-Ser (bases 222–227 of SEQ ID NO:7 (FIG. 5A)), and the coding sequence for the linker region of Ang1 (bases 228–296 of SEQ ID NO:7 (FIG. 5A)) followed by fibrinogen domain of Ang1 (FD) (bases 250–949 of SEQ ID NO:7 (FIGS. 5A–5C)).

Example 8

Characterization of Chimeric-Ang1 Protein—Molecular Weight Analysis

The predicted molecular weights for native Ang1, GCN4/CC-Ang1/FD, CMP/CC-Ang1/FD and COMP/CC-Ang1/FD under reduced state were determined using the Swiss-PROT Program. Predicted weights of FLAG-tagged native Ang1, GCN4/CC-Ang1/FD, CMP/CC-Ang1/FD and COMP/CC-Ang1/FD are 58810.82 Da, 32044.28 Da, 33330.88 Da and 33522.96 Da, respectively. There are five N-linked glycosylation sites in native Ang1, while there is one predicted N-linked glycosylation site in each of GCN4/CC-Ang1/FD, CMP/CC-Ang1/FD and COMP/CC-Ang1/FD. These predicted N-linked glycosylation sites could potentially increase the molecular weight by approximately 2500 Da/site. Thus, the predicted molecular weights for native Ang1, GCN4/CC-Ang1/FD, CMP/CC-Ang1/FD and COMP/CC-Ang1/FD under reducing conditions are approximately, 71.3 kDa, 34.5 kDa, 35.8 kDa, and 36.0 kDa, respectively. Subsequent SDS PAGE analyses (FIG. 8) of COS cell-derived protein described infra confirmed these approximate molecular weights. Molecular weights of native Ang1 (~75 kDa), GCN4/CC-Ang1/FD (~40 kDa), CMP/CC-Ang1/FD (~43 kDa), and COMP/CC-Ang1/FD (~44 kDa) were determined under reducing conditions.

Figure 8:
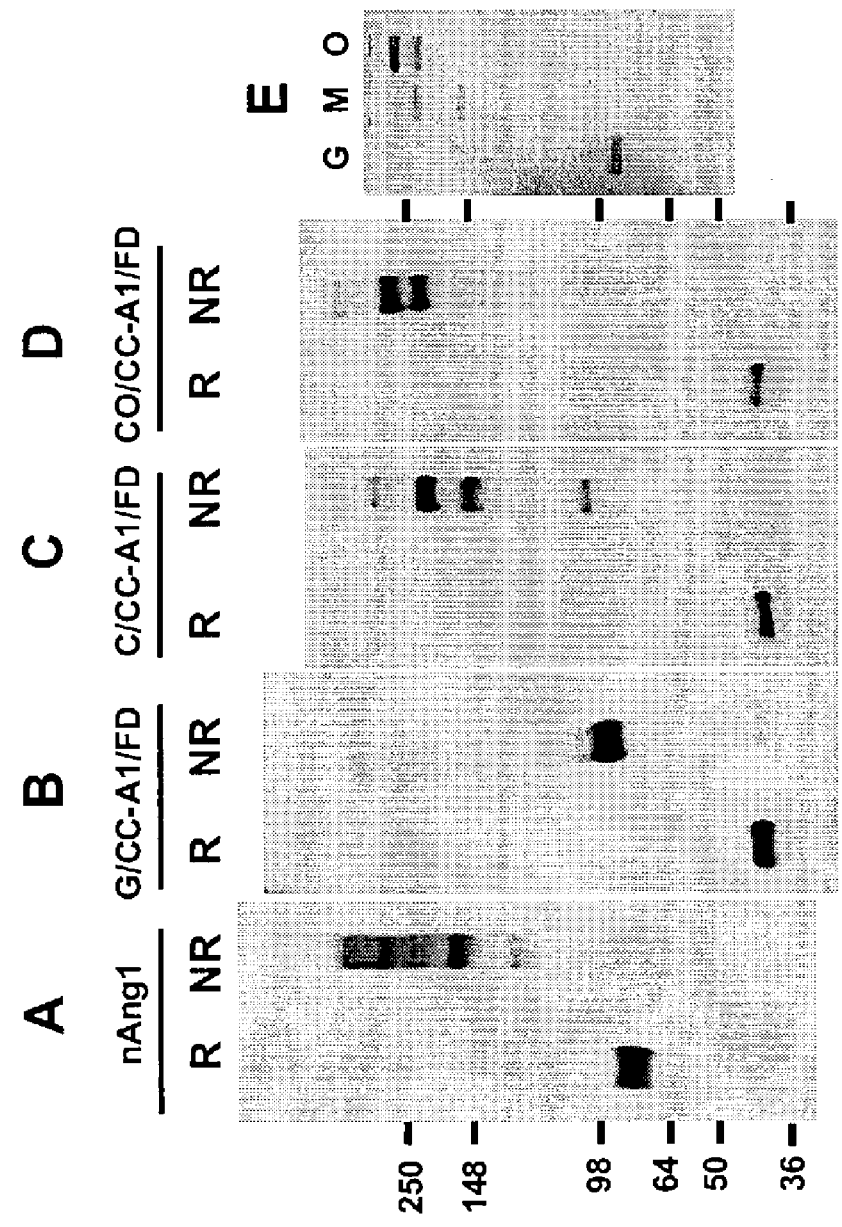
FIGS. 8A–8E show molecular weight analysis of recombinant native Ang1 (nAng1), GCN4/CC-Ang1/FD (G/CC-A1/FD or G), CMP/CC-Ang1/FD (C/CC-A1/FD or M), and COMP/CC-Ang1/FD (CO/CC-A1/FD or O) under reducing (R) and non-reducing (NR) conditions. In (A–D), 100 ng of each recombinant protein (reduced and non-reduced) is separated by 4–15% sodium dodecyl sulfate-polyacrylamide gel electrophoresis (SDS-PAGE), and electro-blotted to nitrocellulose membranes. The nitrocellulose membranes were Western blotted with anti-FLAG M1 antibody, washed, and incubated with horseradish peroxidase-conjugated secondary antibody. Signals were visualized by chemiluminescent detection according to the manufacturer's protocol (Amersham Pharmacia Biotech) and chemiluminescence scanner (LAS-1000, Fuji Film, Tokyo). In (E), 500 ng of each recombinant protein (non-reduced) is separated by 7% SDS-PAGE, and stained with Coomassie blue. Molecular weight marker sizes shown (left bars with numbers (kDa); right bars without numbers) were used to estimate molecular masses.

Variable sizes of native Ang1 and the expected size of GCN4/CC-Ang1/FD (~80 kDa) were shown under non-reducing conditions. However, CMP/CC-Ang1/FD (~140 kDa and ~180 kDa) and COMP/CC-Ang1/FD (~180 kDa and ~250 kDa) exhibited an unexpectedly large molecular weight under non-reducing conditions as compared with the expected molecular weights of recombinant CMP/CC-Ang1/FD (~135 kDa) and COMP/CC-Ang1/FD (~220 kDa) were shown under the non-reducing condition (FIG. 8).

Example 9

Expression Level in Cos Cells

Recombinant proteins of native Ang1, GCN4/CC-Ang1/FD, CMP/CC-Ang1/FD, and COMP/CC-Ang1/FD were assayed by transient expression in COS-7 cells (American Type Culture Collection, Manassas, Va.) using Effectene (a liposome) transfection method according to manufacturer's instructions (Qiagen, Inc.). Briefly, COS-7 cells were grown on gelatin-coated 100 mm dishes with Dulbecco's modified Eagle's medium (DMEM) with 10% FBS at 37° C. in 5% $CO_2$ atmosphere. About 40–50% confluent dishes of COS-7 cells were used for transfection. Effectene transfection reagents were mixed with DNA-Enhancer mixture. After 10 min incubation for transfection-complex formation, the transfection complexes were added onto the cells and the cells were incubated with DMEM with 5% FBS at 37° C. in 5% $CO_2$ atmosphere. The supernatant was harvested from transfected cells after 48–60 hr.

Example 10

Purification of COS Cell Line Supernatant

Because the recombinant proteins contain FLAG sequence, purification is relatively simple and straightforward using anti-FLAG M1 antibody-agarose affinity gel column chromatography (Sigma-Aldrich, Inc.). Briefly, anti-FLAG M1 antibody-agarose gel was washed with 0.1 M glycine/HCI (pH 3.5) and equilibrated with 1×TBS buffer (50 mM Tris, 150 mM NaCl, pH 7.4). The supernatant containing each recombinant protein was passed through a column filled with anti-FLAG M1 antibody-agarose gel. After triple passage of the supernatant, the column was washed with 1×TBS buffer containing 1 mM $CaCl_2$. The recombinant protein bound to the M1 gel was eluted with elution buffer containing 1×TBS and FLAG peptide (Sigma-Aldrich, Inc.). The relatively easy purification of the recombinant proteins provides a distinct advantage over purifying the parent protein, angiopoietin-1, which requires a highly extensive and labor-intensive purification scheme. After purification of COS-7 supernatants, recombinant proteins were quantitated using conventional Bradford method with DU 800 spectrophotometer (Beckman, Inc.) and confirmed with Coomassie blue staining of SDS-PAGE gel. These analyses showed that 100–200 µg of each recombinant protein/liter of COS-7 cell supernatant was obtained, which represents moderate level of expression.

COS-7 cell supernatant yielded approximately 1 mg each of purified native Ang1, GCN4/CC-Ang1/FD, CMP/CC-Ang1/FD and COMP/CC-Ang1/FD that were used in the studies described infra to further characterize the protein.

Example 11

Receptor Binding Analysis of COS Cell-Derived Chimeric-Ang1

Figure 9:
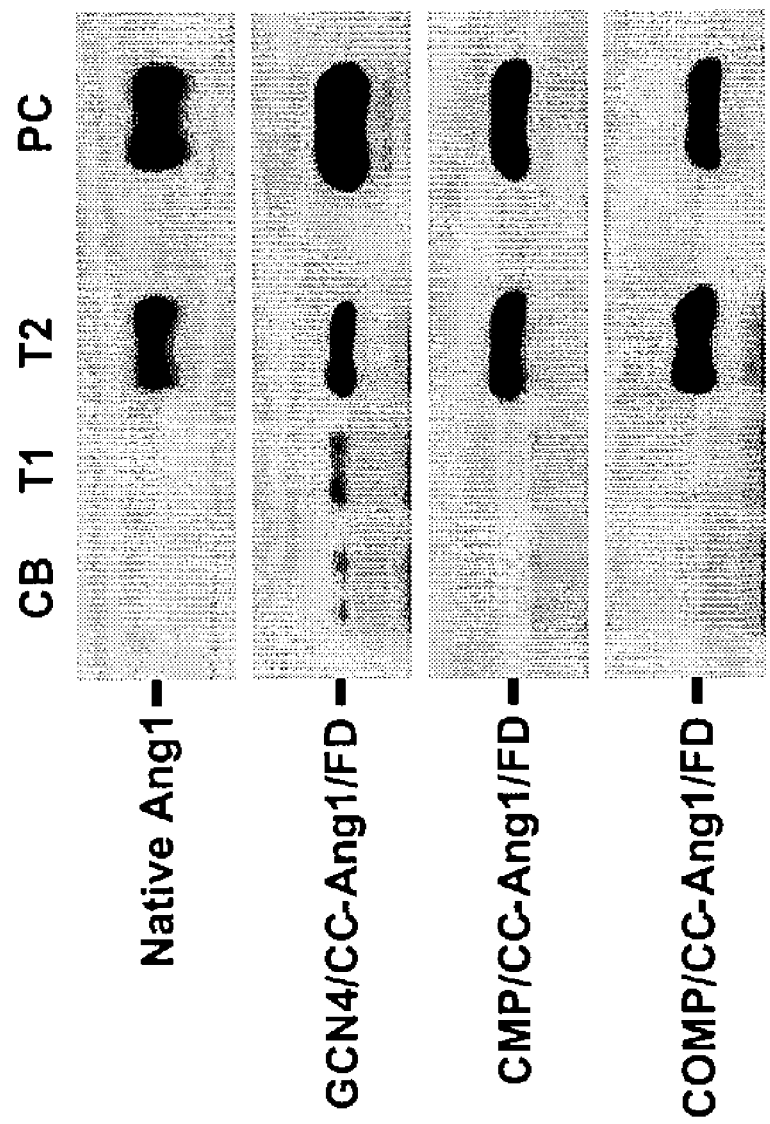
FIG. 9 shows in vitro binding assay between recombinant native Ang1, GCN4-Ang1/FD, CMP-Ang1/FD, or COMP-Ang1/FD and soluble Tie1-Fc (sTie1-Fc, T1) and soluble Tie2-Fc (sTie2-Fc, T2). Twenty nanograms of each protein was incubated with 100 ng of sTie1-Fc or sTie2-Fc for 4 hr, and then, protein-A conjugated agarose beads were added. The precipitate was separated by 10% SDS-PAGE, and electro-blotted on to nitrocellulose membranes. The nitrocellulose membranes were Western blotted with anti-FLAG M1 antibody, washed, and incubated with horseradish peroxidase-conjugated secondary antibody. Signals were visualized by chemiluminescent detection according to the manufacturer's protocol (Amersham Pharmacia Biotech) and chemiluminescence scanner (LAS-1000, Fuji Film, Tokyo). CB, control buffer; PC, positive control of same amount of each recombinant protein without binding.
Figure 10:
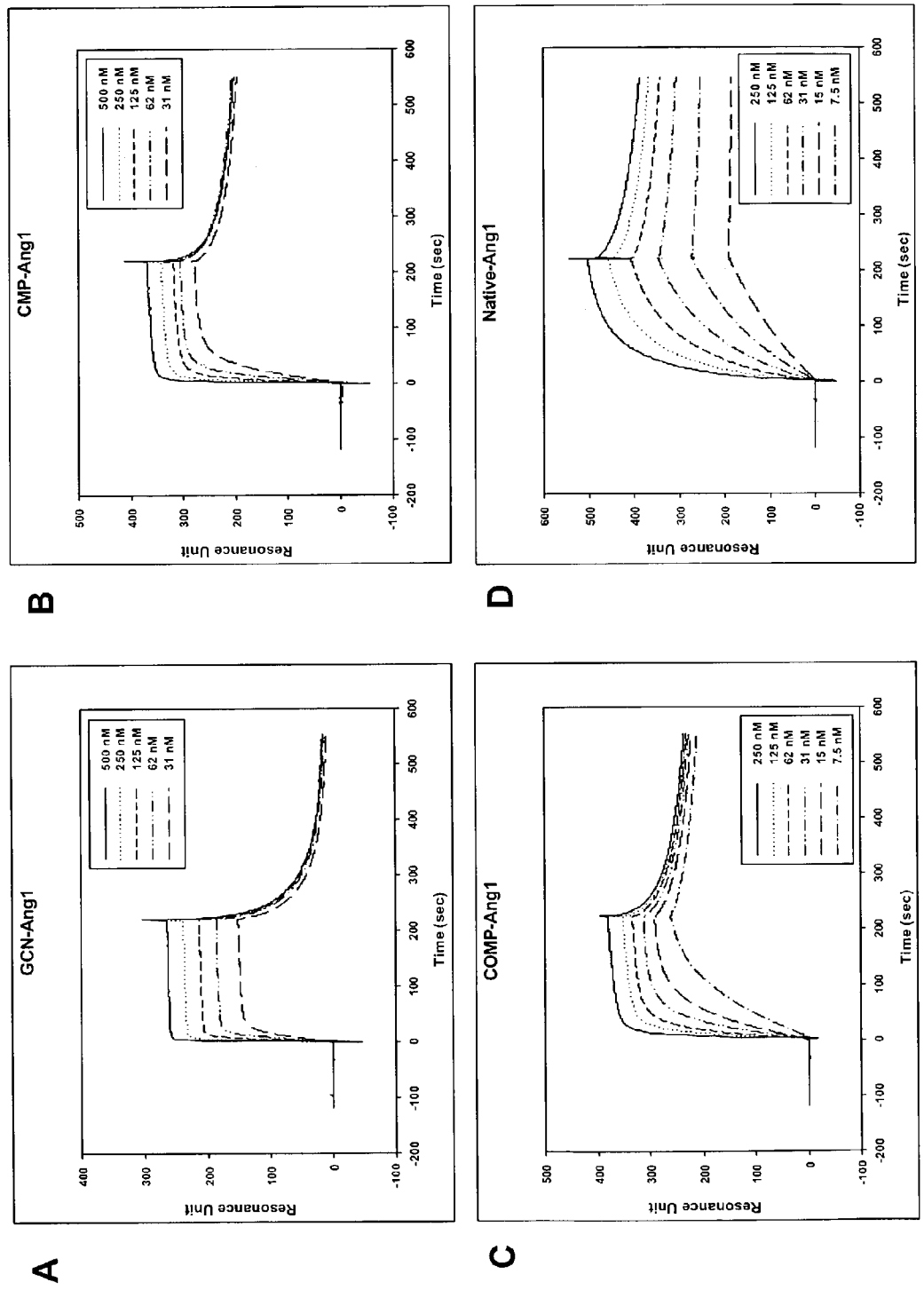
FIGS. 10A–10D show in vitro binding assay between recombinant native Ang1, GCN4-Ang1/FD, CMP-Ang1/FD, or COMP-Ang1/FD and immobilized soluble Tie2-Fc using Biacore assay. Each recombinant protein was passed over a Biacore sensor chip that had extracellular domain of Tie2-Fc and Fc protein covalently coupled to it, followed by dissembling in absence of the recombinant proteins. Concentrations of the recombinant proteins are shown in each panel. Specificity of binding was assessed by substracting Fc protein binding value from Tie2-Fc binding value during the measurement. Binding of the sensor chip is provided in resonance units (RUs). Maximal binding of each recombinant protein was observed at different concentrations. Binding of (A) GCN4-Ang1/FD and (B) CMP-Ang1/FD were saturated at about 30 nM, while (C) COMP-Ang1/FD, and (D) native Ang1 binding saturation point was reached at over 125 nM. The binding affinity of GCN4-Ang1/FD, CMP-Ang1/FD, COMP-Ang1/FD, and native Ang1 were estimated at 158.5 nM, 67 nM, 20.5 nM, and 7.5 nM ($K_D$, dissociation constant), respectively.
Figure 11:
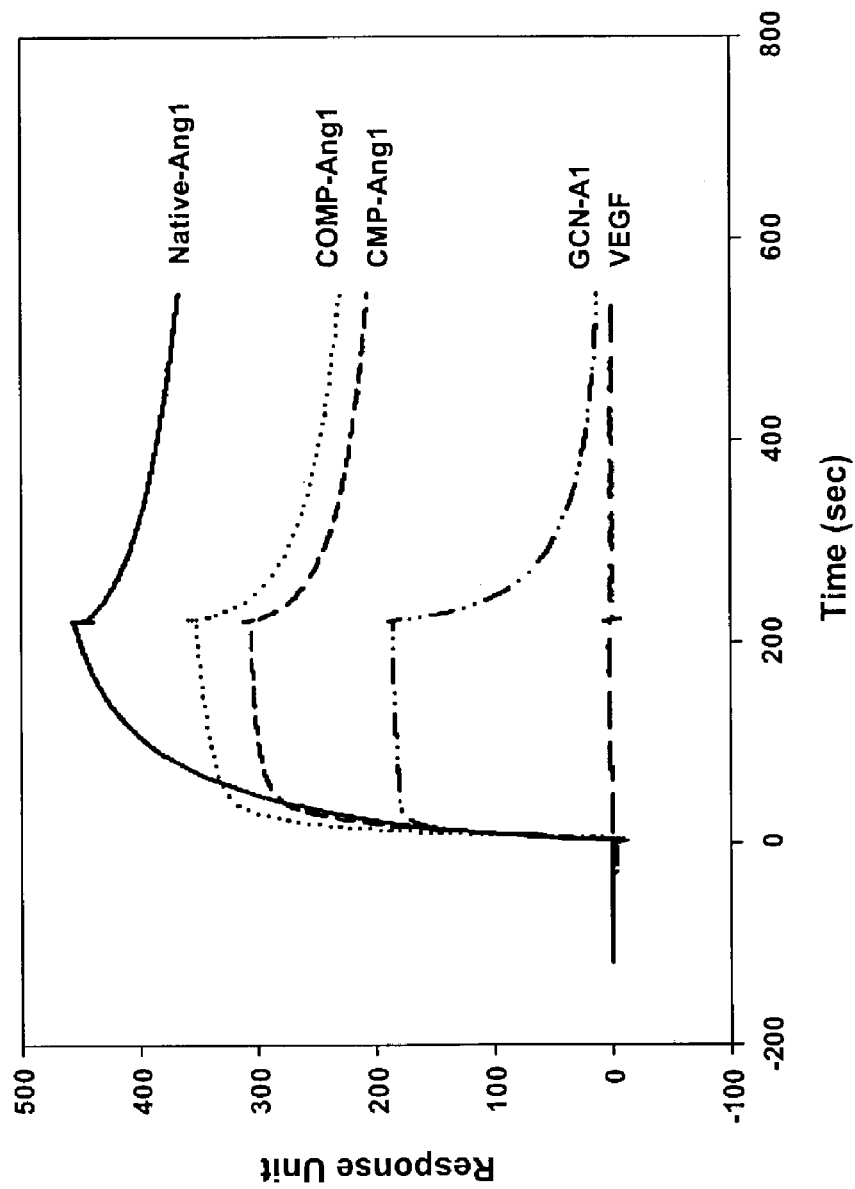
FIG. 11 shows comparison of GCN4-Ang1/FD, CMP-Ang1/FD, COMP-Ang1/FD, and native Ang1 binding characteristics at 60 nM concentration.

Binding analysis of GCN4/CC-Ang1/FD, CMP/CC-Ang1/FD, and COMP/CC-Ang1/FD to soluble Tie2-Fc receptor was performed using in vitro binding assay and Biacore assay. In-vitro standard binding assays revealed that GCN4/CC-Ang1/FD, CMP/CC-Ang1/FD, and COMP/CC-Ang1/FD bind to soluble Tie2 receptor (FIG. 9).

Twenty nanograms of each recombinant chimeric-Ang1 protein and 100 ng of soluble Tie 1-Fc or soluble Tie2-Fc were incubated in 500 µl Tris-buffer solution (50 mM Tris, 100 mM NaCl, pH 7.4) containing 0.02% TritonX-100 at 4° C. for 2 hr. Then, 20 µl of protein-A agarose beads (Oncogene) was added and incubated for another 1 hr at 4° C. The protein-A conjugated samples were washed twice with 1 ml of Tris-buffer containing 0.02% TritonX-100. The samples were eluted with sample buffer, and heat-denatured. The samples were further separated by 10% SDS-PAGE, and electro-blotted on to nitrocellulose membranes, and Western blotted with anti-FLAG M1 antibody to detect the bound recombinant chimeric-Ang1, and further washed and incubated with horseradish peroxidase-conjugated secondary antibody. Signal was visualized by chemiluminescent detection according to the manufacturer's protocol (Amersham Pharmacia Biotech) using chemiluminescence scanner (LAS-1000, Fuji Film, Tokyo). See FIG. 9. Approximately 75%, 20%, 95% or 100% of native Ang1, GCN4-Ang1/FD, CMP-Ang1/FD, and COMP-Ang1/FD, respectively, bound to sTie2-Fc. In contrast, none of them bound to sTie1-Fc.

Alternatively, to determine whether the COS-7 cell-derived recombinant proteins of native Ang1, GCN4/CC-Ang1/FD, CMP/CC-Ang1/FD and COMP/CC-Ang1/FD could bind to Tie-2 receptor, standard Biacore analysis was performed by BIA2000 (BIAcore, Inc.). Briefly, 600 ng of Tie-2-Fc receptor protein (R&D Inc), which is a fusion protein composed of the ectodomain of Tie-2 receptor and Fc domain of human IgG1, was immobilized on a Biacore chip (Sensor Chip CM5). As a control, 600 ng of Fc protein, which had only the Fc domain of human IgG1, was also immobilized on the same chip. The binding affinity was obtained by subtracting the response value using Fc protein from the values obtained using the Tie-2-Fc protein.

The recombinant proteins including native Ang1, GCN4/CC-Ang1/FD, CMP/CC-Ang1/FD and COMP/CC-Ang1/FD were passed over the chip to allow binding between Tie-2 receptor ectodomain and the recombinant proteins. The binding step was followed by a dissociation step that allowed the bound proteins to dissociate from the Tie-2 receptor ectodomain. GCN4/CC-Ang1/FD was completely dissociated from the immobilized Tie-2 receptor ectodomain within 5 minutes, while CMP/CC-Ang1/FD, COMP/CC-Ang1/FD, and native Ang1 was not as easily dissociated, implying that there is a strong interaction between CMP/CC-Ang1/FD, COMP/CC-Ang1/FD, native Ang1 and Tie-2 receptor ectodomain. To dissociate these proteins from the receptor, various HCl solutions (pH 4.0–2.0) and high salt (1M NaCl) solution were passed over the chip. However, these solutions were not able to disrupt the interaction between Tie-2 receptor ectodomain and the recombinant proteins, indicating that there is a strong interaction between the Tie-2 receptor ectodomain and the recombinant proteins (CMP/CC-Ang1/FD, COMP/CC-Ang1/FD, and native Ang1) See FIGS. 10A–10D and 11.

In addition, association phase of native Ang1 was slower than GCN4-Ang1/FD, CMP-Ang1/FD, COMP-Ang1/FD, implying that modification of coiled-coil domain of the native Ang1 increased its association constant to Tie2 receptor, and that high affinity of the native Ang1 came from its slow dissociation.

Example 12

Tie2 Phosphorylation Assay

Figure 12:
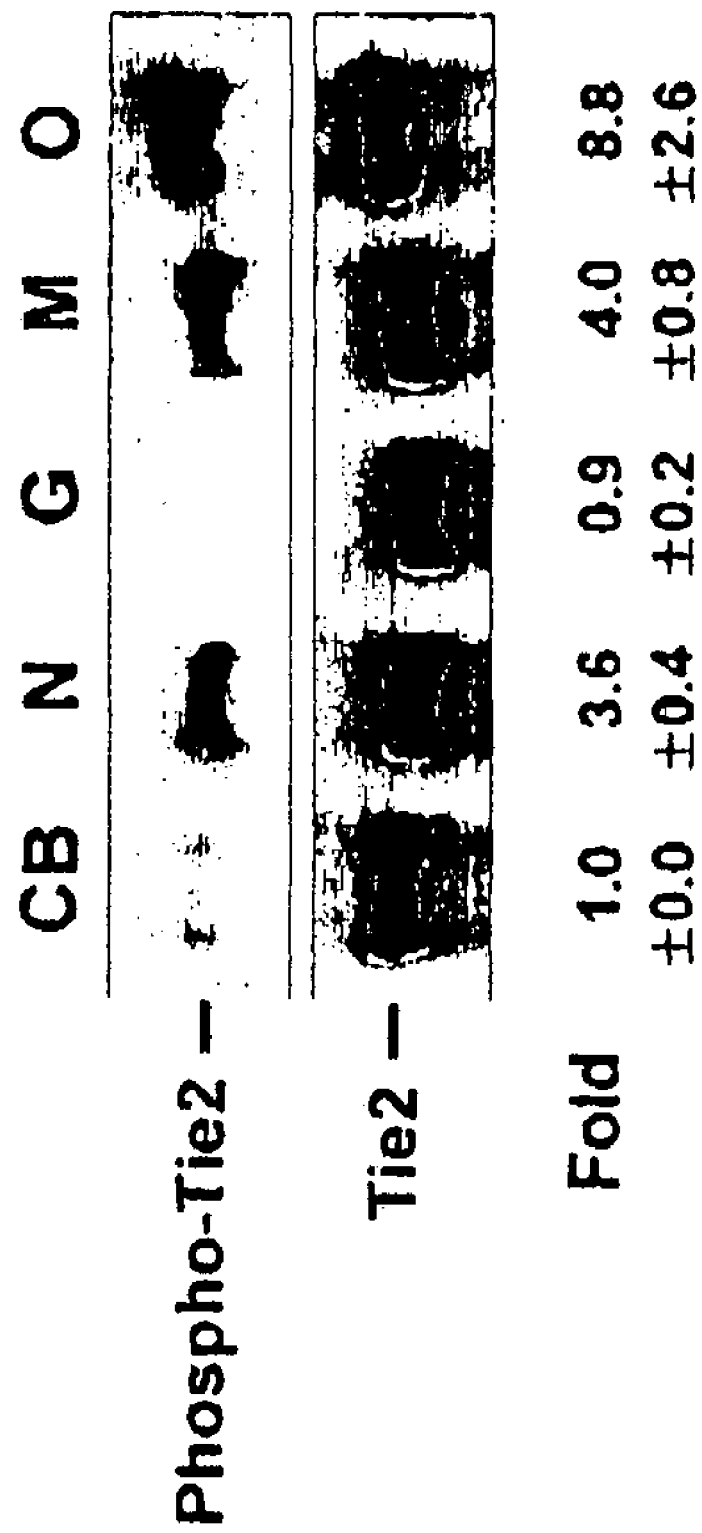
FIG. 12 shows comparison of native Ang1, GCN4-Ang1/FD, CMP-Ang1/FD, and COMP-Ang1/FD in a Tie2 phosphorylation assay using human umbilical venous endothelial cells (HUVECs). HUVECs were incubated with control buffer (CB), and 200 ng of native Ang1 (N), GCN4-Ang1/FD (G), CMP-Ang1/FD (M), or COMP-Ang1/FD (O) for 10 min. The cells were harvested in extraction buffer, and 0.5 mg of protein was used for immunoprecipitation. Tie2 proteins in the samples were immunoprecipitated with anti-Tie2 antibody and collected. Immunoprecipitated samples were Western blotted with anti-phospho-tyrosine antibody (upper panel), and the membrane was re-blotted with anti-Tie2 antibody to verify equal loading of protein in each lane (lower panel). Results were similar in three independent experiments. Fold: Densitometric analyses are presented as the relative ratio of phospho-Tie2 to Tie2. The relative ratio measured in CB is arbitrarily presented as 1.
Figure 14:
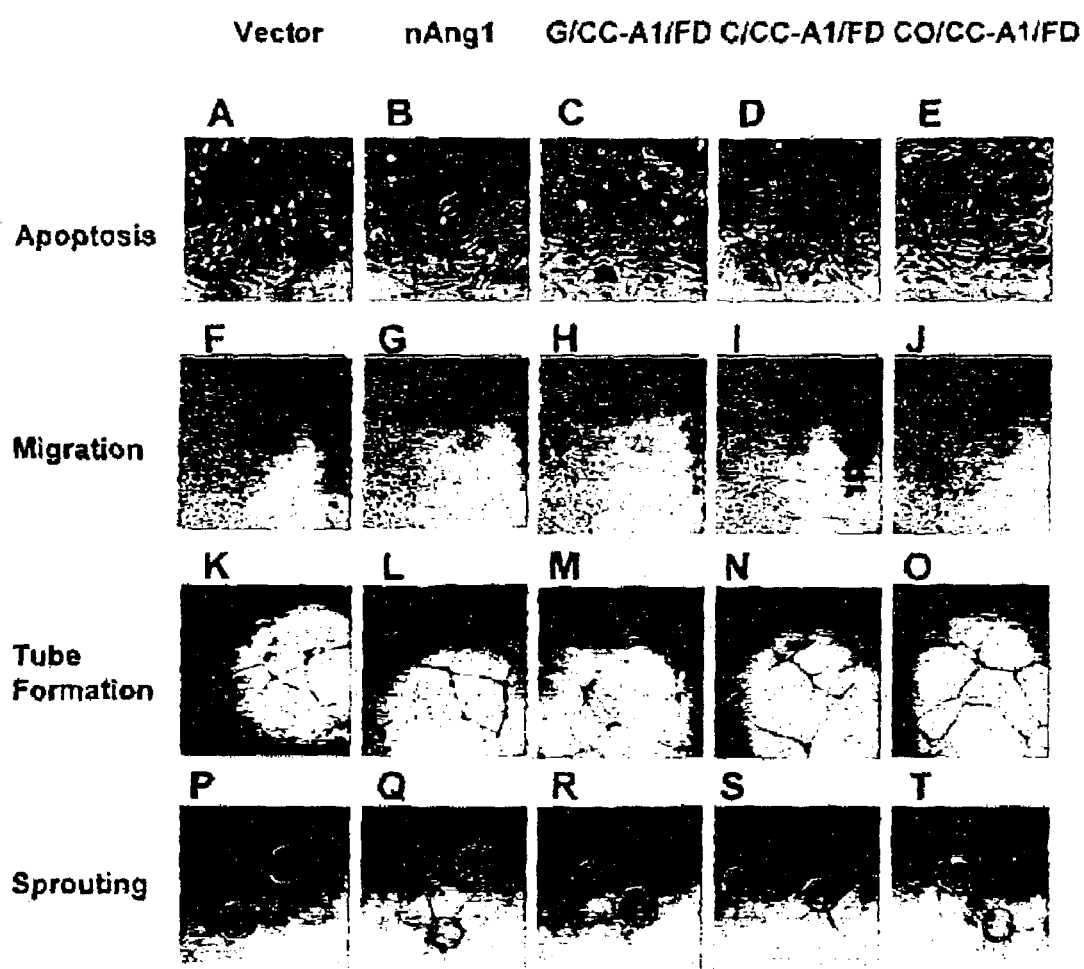
FIGS. 14A–14T show a comparison between native Ang1GCN4-Ang1/FD, CMP-Ang1/FD, and COMP-Ang1/FD in survival, migration, tube formation and sprouting activities of primary cultured endothelial cells. Representative photographs are shown. Native Ang1 and CMP/CC-Ang1/FD induced notable increase in survival, migration, tube formation and sprouting activities. Notably, COMP/CC-Ang1/FD-induced survival, migration, tube formation and sprouting activities were greater than native Ang1- and CMP/CC-Ang1/FD-induced survival, migration, tube formation and sprouting activities. However, GCN4/CC-Ang1/FD did not appear to exhibit any notable change in survival, migration, tube formation or sprouting activities.

Human umbilical vein endothelial cells (HUVECs) were prepared from human umbilical cords by collagenase digestion and maintained as previously described (Kim et al., 2000 Circ. Res. 86: 24–29). The primary cultured cells used for the biochemical assays were between passages 2 and 3. Primary cultured HUVECs were incubated with control buffer, and 200 ng of native Ang1, GCN4/CC-Ang1/FD, CMP/CC-Ang1/FD, or COMP/CC-Ang1/FD for 10 min. The cells were harvested in extraction buffer, and 0.5 mg of protein was used for immunoprecipitation. Tie2 proteins in the sample was immunoprecipitated with anti-Tie2 antibody and collected. Immunoprecipitated samples were Western blotted with anti-phospho-tyrosine antibody (upper band), and the membrane was re-blotted with anti-Tie2 antibody (lower band) to verify equal loading of protein in each lane. The assay revealed that COMP/CC-Ang1/FD-induced Tie2 phosphorylation (~8.8 fold) is much higher than phosphorylation induced by native Ang1 (~3.6 fold) or CMP/CC-Ang1/FD (~4.0 fold). However, GCN4/CC-Ang1/FD did not change Tie2 phosphorylation (FIG. 12).

Example 13

AKT (SER473) Phosphorylation Assay

HUVECs were incubated with control buffer, and 200 ng of native Ang1, GCN4/CC-Ang1/FD, CMP/CC-Ang1/FD or COMP/CC-Ang1/FD for 15 min. Alternatively, HUVECs were incubated with control buffer and different amounts of COMP/CC-Ang1/FD. HUVECs were also incubated with 200 ng of COMP/CC-Ang1/FD for different times. After treatment, cell lysates were harvested. Each lane contained 50 μg of total protein from the cell lysates. Western blots were probed with anti-phospho-Akt (Ser473) antibody. The blot was reprobed with anti-Akt antibody (lower bands) to verify equal loading of protein in each lane. The assay revealed that COMP/CC-Ang1/FD-induced Akt (Ser 473) phosphorylation (9.7 fold) is greater than Akt (Ser 473) phosphorylation induced by native Ang1 (3.7 fold) or CMP/CC-Ang1/FD (3.3 fold). However, GCN4/CC-Ang1/FD does not change Akt (Ser 473) phosphorylation. COMP/CC-Ang1/FD-induced Akt (Ser 473) phosphorylation occurs in a dose-dependent manner and persists up to 60 min (FIGS. 13A–13C, upper bands).

Example 14

Apoptosis Assay

To induce apoptosis, HUVECs were plated onto gelatinized 24-well plates ($7 \times 10^4$ cells per well) in M-199 containing 20% FBS and incubated for 12 hr. The wells were extensively washed with PBS, and the medium was changed to serum-free M-199 containing control buffer, 200 ng/ml of native Ang1, GCN4-Ang1/FD, CMP-Ang1/FD, or COMP-Ang1/FD, and incubated for 30 hr. Floating apoptotic cells were collected with 2 washes in PBS. Adherent cells were collected by trypsinization. All cells were stained with Annexin V FLUOS staining kit (Roche Molecular Biochemicals, Mannheim, Germany) for 15 min at 20° C. Following staining of Annexin-V and propidium iodide (PI), the cells were analyzed on a flow cytometer and data were analyzed with CellQuest software (Becton Dickinson). The results were: Native Ang1 (about 47% increased cell survival), GCN4/CC-Ang1/FD (about 12% increased cell survival), CMP/CC-Ang1/FD (about 55% increased cell survival) and COMP/CC-Ang1/FD (about 71% increased cell survival). FIGS. 14A–14E. See also Table 1.

Table 1. Biological activities of native and chimeric Ang1 proteins in endothelial cells.

|  | Apoptosis | Migration | Tube length | Sprouting |
|---|---|---|---|---|
| Vector | 32.4 ± 5.6 | 56.4 ± 3.5 | 28.4 ± 4.2 | 35.5 ± 7.5 |
| Native Ang1 | 17.2 ± 2.3 | 104.7 ± 4.6 | 42.4 ± 4.8 | 91.5 ± 10.5 |
| GCN4/CC-Ang1/FD | 28.6 ± 4.3 | 68.0 ± 7.2 | 25.6 ± 3.3 | 42.5 ± 8.6 |
| CMP/CC-Ang1/FD | 14.7 ± 2.2 | 116.2 ± 4.2 | 43.6 ± 4.6 | 78.8 ± 8.8 |
| COMP/CC-Ang1/FD | 9.4 ± 1.4 | 145.5 ± 6.3 | 55.8 ± 6.9 | 121.5 ± 11.5 |

Example 15

In Vitro Wounding Migration Assay

Cell migration assay was carried out according to Sato and Rifkin (1989, J. Cell. Biol. 109:309–315) with slight modification. Primary cultured HUVECs were grown to confluence in 30 mm diameter dish in 1 ml of normal growth medium. Wounds were made in the monolayer by scratching the cell layer with a double-edged razor blade and the injury line marked. The scratch extended over an area 5–7 mm wide. After wounding, the cultures were washed immediately with serum-free medium to remove cell debris and any soluble factors that had been released. The wounded cells were further incubated in serum free medium with control buffer or 200 ng/ml of native Ang1, GCN4/CC-Ang1/FD, CMP/CC-Ang1/FD, or COMP/CC-Ang1/FD. HUVECs were allowed to migrate for 10 hr and were rinsed with PBS, followed by fixing with absolute methanol and staining with Giemsa. Migration was quantitated by counting the number of cells that moved beyond the reference line. All experiments were performed in triplicate. The results were: Native Ang1 (about 1.86 fold increase of cell migration), GCN4/CC-Ang1/FD (about 1.20 fold increase of cell migration), CMP/CC-Ang1/FD (about 2.06 fold increase of cell migration) and COMP/CC-Ang1/FD (about 2.58 fold increase of cell migration). See FIGS. 14F–14J. See also Table 1.

Example 16

Tube Formation Assay

Matrigel (Sigma-Aldrich Inc.) was thawed overnight at 4° C. and mixed to homogeneity using cooled pipette tips. Matrigel was added to the 24-well tissue culture plate (250 µl/well) at 4° C. The 24-well plate was brought to a 37° C. cell culture incubator and incubated for 1 hr to allow the Matrigel to solidify. HUVECs were trypsinized, counted, resuspended in serum free M-199 medium, and added on Matrigel ($1\times10^5$ cells/well) in the presence of control buffer, and 200 ng/ml of native Ang1, GCN4/CC-Ang1/FD, CMP/CC-Ang1/FD or COMP/CC-Ang1/FD. Cells were incubated for 12 hr to allow capillary-like structure to form. After 12 hr, the wells were washed with PBS, fixed for 30 min in 0.5% glutaraldehyde, and the length of capillary-like tubes were quantified using Image Pro-Express Software (Cyber Media). The results were: Native Ang1 (about 1.49 fold increase of tube formation), GCN4/CC-Ang1/FD (about 0.90 fold increase of tube formation), CMP/CC-Ang1/FD (about 1.53 fold increase of tube formation) and COMP/CC-Ang1/FD (about 1.96 fold increase of tube formation). See FIGS. 14K–14O. See also Table 1.

Example 17

Sprouting Assay

Cell sprouting assay in porcine pulmonary artery endothelial cells (PPAECs) was performed as previously described (Kim et al., 2000, Circ. Res. 86:952–959). Briefly, PPAECs were grown to confluence on microcarrier beads (diameter 175 µm; Sigma) and placed in a 2.5 mg/ml fibrinogen gel containing 2.0% heat-inactivated FBS and the indicated recombinant protein. Fibrin gels were incubated in DMEM with a daily addition of the same amount of recombinant protein. After 3 days, two independent investigators with no knowledge of which is the experimental or control counted the number of sprouts using an inverted microscope. The number of endothelial sprouts with length exceeding the diameter of the microcarrier beads (175 µm) per 50 microcarrier beads was counted. Inter-investigator variation was <5%. The mean number from the two investigators was used to estimate the number of sprout formation. The results were: Native Ang1 (about 2.58 fold increase of sprouting), GCN4/CC-Ang1/FD (about 1.20 fold increase of sprouting), CMP/CC -Ang1/FD (about 2.22 fold increase of sprouting) and COMP/CC-Ang1/FD (about 3.42 fold increase of sprouting). See FIGS. 14P–14T. See also Table 1.

Example 18

Biophysical and Biochemical Assay

Secretion: Native Ang1, GCN4/CC-Ang1/FD, CMP/CC-Ang1/FD, and COMP/CC-Ang1/FD are secreted from COS cells. The media and cells are harvested at 48 hr after the transfection of each gene. The protein levels are examined by Western-blot analysis.

Purification: Native Ang1, GCN4/CC-Ang1/FD, CMP/CC-Ang1/FD, and COMP/CC-Ang1/FD are purified and tested for their stability, aggregation and stickiness.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A coiled coil chimeric molecule comprising a coiled-coil domain of cartilage oligomeric matrix protein linked to a Tie2 receptor binding domain which is a fibrinogen-like domain of angiopoietin-1.

2. A soluble biologically active multimer comprising the coiled coil chimeriic molecule according to claim 1.

3. The multimer according to claim 2, which is a dimer, trimer, tetramer, pentamer, hexamer, heptamer, octamer, nanomer or decamer.

4. A method of promoting endothelial cell migration in vitro comprising contacting the coiled coil chimeric molecule of claim 1, to a population of cells that express Tie2 receptors, which results in endothelial cell migration.

* * * * *